United States Patent
Kamal et al.

(10) Patent No.: US 9,783,537 B2
(45) Date of Patent: Oct. 10, 2017

(54) 3-(4-ETHYLNYLPHENYL) PYRIDOPYRIMIDINONE COMPOUNDS AND PROCESS FOR PREPARATION THEREOF USEFUL AS POTENTIAL ANTICANCER AGENTS

(71) Applicant: Council of Scientific & Industrial Research, New Delhi (IN)

(72) Inventors: Ahmed Kamal, Andhra Pradesh (IN); Ranjita Nayak, Andhra Pradesh (IN); Farheen Sultana, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/912,755

(22) PCT Filed: Oct. 15, 2013

(86) PCT No.: PCT/IN2013/000626
§ 371 (c)(1),
(2) Date: Feb. 18, 2016

(87) PCT Pub. No.: WO2015/025326
PCT Pub. Date: Feb. 26, 2015

(65) Prior Publication Data
US 2016/0222006 A1 Aug. 4, 2016

(30) Foreign Application Priority Data
Aug. 19, 2013 (IN) .......................... 2443/DEL/2013

(51) Int. Cl.
*C07D 471/04* (2006.01)

(52) U.S. Cl.
CPC ................................. *C07D 471/04* (2013.01)

(58) Field of Classification Search
None
See application file for complete search history.

(56) References Cited

FOREIGN PATENT DOCUMENTS

WO  WO 2007/134986  11/2007
WO  WO 2012/111017  8/2012

OTHER PUBLICATIONS

International Search Report & Written Opinion, International Application No. PCT/IN2013/000626, Apr. 17, 2014, 14 pages.
M. Baghbanzadeh et al., "Parallel microwave synthesis of 2-styrylquinazolin-4(3H)-ones in a high-throughput platform using HPLC/GC vials as reaction vessels," J. Comb. Chem. 11(4):676-684, 2009.
L. Cordeu et al., "Biological profile of new apoptotic agents based on 2,4-pyridol[2,3-d]pyrimidine derivgatives," Bioorganic and Medicinal Chemistry 15:1659-1669, 2007.
A. Elgohary et al., "Green and efficient synthesis of some pyrido [2,3-D] pyrimidin-4(3H)-one derivatives via iodine catalyst in aqueous media and evaluation the synthesized compounds as anticancer," Science Journal of Chemistry 1(1), Apr. 2, 2013, pp. 1-6.
X.-N. Guo et al., "In vitro pharmacological characterization of TKI-28, a broad-spectrum tyrosine kinase inhibitor with anti-tumor and anti-angiogenic effects," Cancer Biology and Therapy 4(10):1125-1132, Oct. 2015.
S. Kamath et al., "Targeting EGFR and HER-2 receptor tyrosine kinases for cancer drug discovery and development," Medicinal Research Reviews 26(5):569-594, 2006.
T. Siu et al., "Discovery of potent and cell-active allosteric dual Akt 1 and 2 inhibitors," Bioorganic and Medicinal Chemistry Letters 18:4186-4190, 2008.

*Primary Examiner* — Emily Bernhardt
(74) *Attorney, Agent, or Firm* — Lathrop Gage LLP

(57) ABSTRACT

The present invention provides 3-(4-ethynylphenyl) pyridopyrimidinone compounds of formula A active as potential anticancer agents. The 3-(4-ethynylphenyl) pyridopyrimidinone compounds of the present application have shown promising anticancer activity in sixty human cancer cell lines.

9 Claims, 2 Drawing Sheets

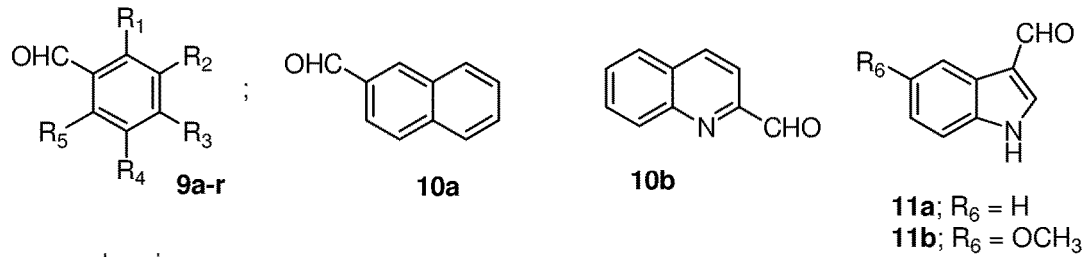

wherein

Figure 2:
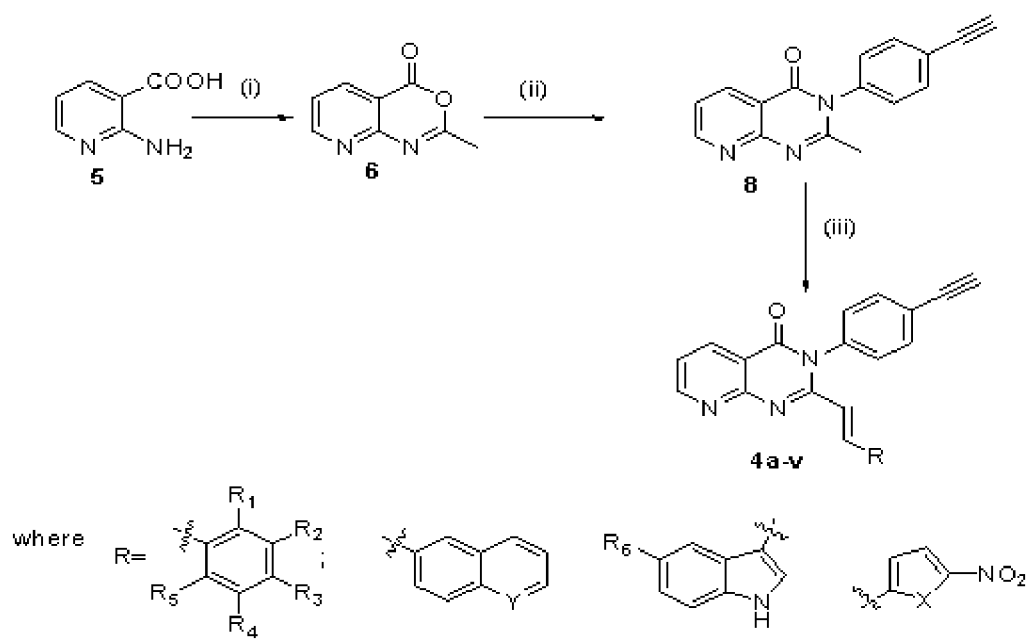

9a: $R_1 = R_2 = R_4 = R_5 = H$; $R_3 = F$
9b: $R_1 = R_2 = R_4 = R_5 = H$; $R_3 = OH$
9c: $R_1 = R_2 = R_4 = R_5 = H$; $R_3 = CF_3$
9d: $R_1 = R_2 = R_4 = R_5 = H$; $R_3 = OCF_3$
9e: $R_1 = R_2 = R_4 = R_5 = H$; $R_3 = Cl$
9f: $R_1 = R_4 = R_5 = H$; $R_2 = R_3 = F$
9g: $R_1 = R_4 = R_5 = H$; $R_2 = F$; $R_3 = Cl$
9h: $R_1 = R_4 = R_5 = H$; $R_2 = F$; $R_3 = OCH_3$
9i: $R_2 = R_4 = R_5 = H$; $R_1 = R_3 = H$
9j: $R_2 = R_3 = R_5 = H$; $R_1 = R_4 = H$
9k: $R_1 = R_4 = R_2 = H$; $R_2 = OCH_3$; $R_3 = OH$
9l: $R_1 = R_4 = R_2 = H$; $R_2 = NO_2$; $R_3 = OH$
9m: $R_1 = R_3 = R_5 = H$; $R_2 = R_4 = OCH_3$
9n:: $R_1 = R_3 = R_4 = H$; $R_2 = R_5 = OCH_3$
9o: $R_1 = R_3 = R_5 = H$; $R_2 = R_4 = OCH_3$
9p:: $R_1 = R_5 = H$; $R_3 = OH$; $R_2 = R_4 = OCH_3$
9m: $R_1 = R_5 = H$; $R_2 = R_3 = R_4 = OCH_3$
9n:: $R_2 = R_4 = H$; $R_1 = R_3 = R_5 = OCH_3$

Structures of substituted aldehydes

FIG. 1

Flow diagram for the preparation of compound of Formula A

3-(4-ETHYLNYLPHENYL) PYRIDOPYRIMIDINONE COMPOUNDS AND PROCESS FOR PREPARATION THEREOF USEFUL AS POTENTIAL ANTICANCER AGENTS

FIELD OF THE INVENTION

The present invention relates to synthesis and biological evaluation of 3-(4-ethynylphenyl) pyridopyrimidinone compounds of formula A as potential anticancer agents and a process for the preparation thereof,

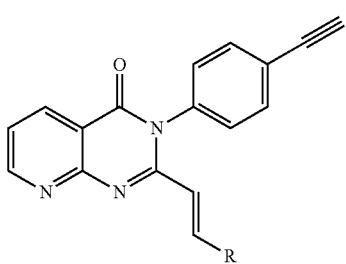

Formula A wherein

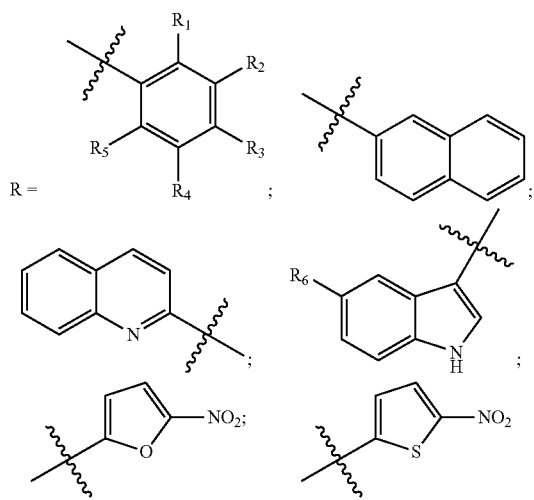

$R_1$ = H, OH, OCH$_3$
$R_2$ = H, OH, CH$_3$, OCH$_3$, NO$_2$
$R_3$ = H, OH, OCH$_3$, F, Cl
$R_4$ = H, OH, CH$_3$, OCH$_3$
$R_5$ = H, OH, CH$_3$, OCH$_3$
$R_6$ = H, OCH$_3$
$R_2 + R_3$ = ——OCH$_2$O——

BACKGROUND OF THE INVENTION

The Erb family of receptors is transmembrane receptor tyrosine kinases involved in a wide range of signal transduction and cellular functions, and have become a very fruitful area for the successful development of drugs to treat cancer. ErbB2 is found to be significantly over expressed in 20-30% of human breast cancers and is associated with a poor prognosis. EGFR (erbB1) has also been targeted for the treatment of cancer, and several agents have been approved with this mode of action. (*Med. Res. Rev.* 2006, 26, 569.)

Pyridopyrimidine nucleus is a pharmacophoric scaffold and represents a class of heterocyclic compounds with a wide range of biological applications. Many of them are widely used as anticonvulsant, sedative, anti-depressive, anti-pyretic agents. Some heterocycles containing pyrido pyrimidine moiety were reported to possess anti-inflammatory, antiviral, antimicrobial, and anti-tumor activities. Other than their biological importance, pyrido pyrimidine derivatives are valuable for the preparation of fused ring compounds, such as triazolopyrimidines, thieno-pyrimidines, thiazolo-pyrimidines, and pyridopyrimidines. It has been noticed that introduction of an 4-ethynyl phenyl ring at 3-position of pyrido pyrimidines core tends to exert profound influence in conferring novel biological activities like anticancer activity in these molecules. Although many methods for synthesizing pyridopyrimidines ring systems have been reported, they continue to receive a great deal attention.

Pyrido[2,3-d]pyrimidine nucleus containing compounds have shown diverse biological profiles, great specificity for individual subgroups of receptor tyrosine kinases and also inhibit non-receptor tyrosine kinases such as Abl, Akt or cyclin kinases. Another target for these derivatives is dihydrofolate reductase inhibition, e.g. piritrexim (*Cancer Biol. Ther.* 2005, 4, 1125-1132).

A number of pyrido[2,3-d]pyrimidine nucleoside analogues have been either used clinically as tumour agents or evaluated in clinical studies. These compounds have been demonstrated to specifically inhibit tyrosine kinases and participating in a number of cellular signaling events including mitogenesis processes. (*Bioorg. Med. Chem.* 2007, 15, 1659-1669).

The PI3K/Akt pathway has attracted much attention in the cancer research community due to its involvement in multiple cell survival, growth, energy metabolism, and proliferation pathways.

Recently a wide range of pyridopyrimidine amines, have been synthesized which were tested against different cell lines which inhibit the phosphorylation of Akt isozymes in C33a cancer cells (*Bioorg. Med. Chem. Lett.* 2008, 18, 4186-4190).

OBJECTS OF THE INVENTION

The main objective of the present invention is to provide 3-(4-ethynylphenyl) pyridopyrimidinone compounds of formula A.

Another objective of the present invention is to provide process for the preparation of 3-(4-ethynylphenyl)pyridopyrimidinone compounds of formula A.

Still another objective of the present invention is to provide 3-(4-ethynylphenyl)pyridopyrimidinone compounds of formula A as potential anticancer agents.

SUMMARY OF THE INVENTION

Accordingly, the present invention provides 3-(4-ethynyl-phenyl)pyridopyrimidinone compounds of formula A Formula A

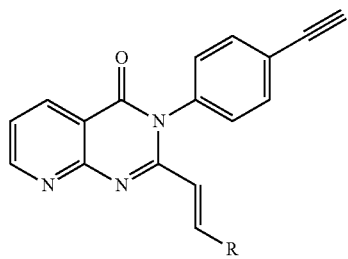

Formula A wherein

R = 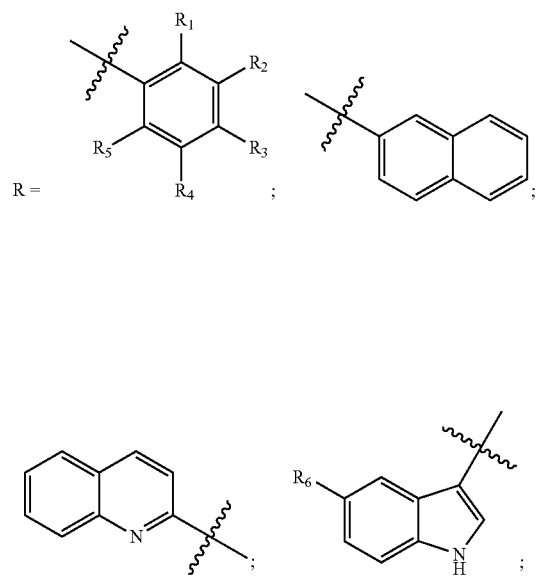

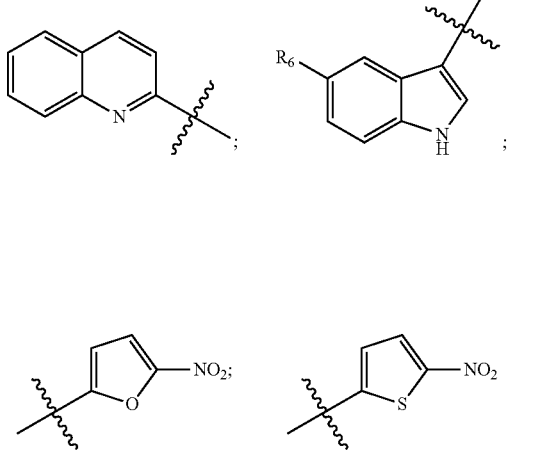

$R_1$ = H, OH, OCH$_3$
$R_2$ = H, OH, CH$_3$, OCH$_3$, NO$_2$
$R_3$ = H, OH, OCH$_3$, F, Cl
$R_4$ = H, OH, CH$_3$, OCH$_3$
$R_5$ = H, OH, CH$_3$, OCH$_3$
$R_6$ = H, OCH$_3$
$R_2$ + $R_3$ = —OCH$_2$O—

In an embodiment of the present invention, structural formulae of the representative groups of formula A are:

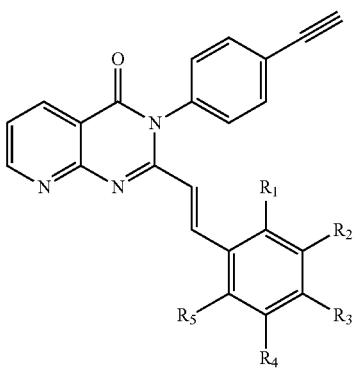

4a-r

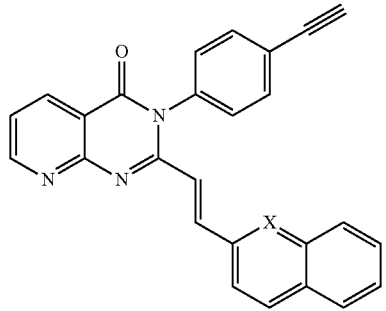

X = H, 4s
X = N, 4t

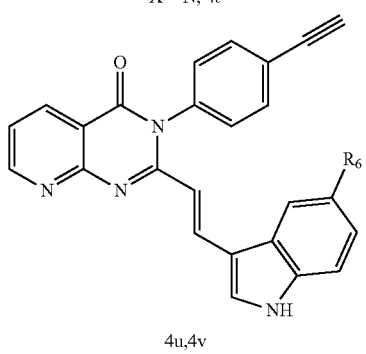

4u,4v

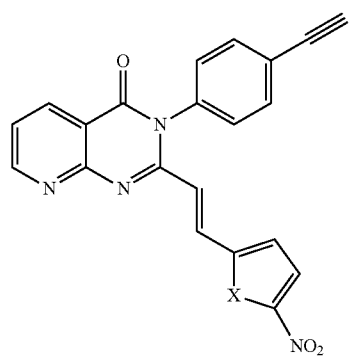

X = O, S
4w,4x $R_1$ = H, OH, OCH$_3$
$R_2$ = H, OH, CH$_3$, OCH$_3$, NO$_2$
$R_3$ = H, OH, OCH$_3$, F, Cl
$R_4$ = H, OH, CH$_3$, OCH$_3$
$R_5$ = H, OH, CH$_3$, OCH$_3$
$R_6$ = H, OCH$_3$
$R_2$ + $R_3$ = —OCH$_2$O—

In another embodiment of the present invention, said compounds are useful as anticancer agents.

In yet another embodiment of the present invention, the chemical formulae of the representative compounds of formula A are:

(E)-3-(4-Ethynylphenyl)-2-(4-fluorostyryl)pyrido[2,3-d]pyrimidin-4(3H)-one (4a)

(E)-3-(4-Ethynylphenyl)-2-(4-hydroxystyryl)pyrido[2,3-d]pyrimidin-4(3H)-one (4b)

(E)-3-(4-Ethynylphenyl)-2-(4-(trifluoromethyl)styryl)pyrido[2,3-d]pyrimidin-4(3H)-one (4c)

(E)-3-(4-Ethynylphenyl)-2-(3-(trifluoromethoxy)styryl)pyrido[2,3-d]pyrimidin-4(3H)-one (4d)

(E)-2-(4-Chlorostyryl)-3-(4-ethynylphenyl)pyrido[2,3-d]pyrimidin-4(3H)-one (4e)

(E)-2-(3,4-Difluorostyryl)-3-(4-ethynylphenyl)pyrido[2,3-d]pyrimidin-4(3H)-one (4f)

(E)-2-(4-Chloro-3-fluorostyryl)-3-(4-ethynylphenyl)pyrido[2,3-d]pyrimidin-4(3H)-one (4g)

(E)-3-(4-Ethynylphenyl)-2-(3-fluoro-4-methoxystyryl)pyrido[2,3-d]pyrimidin-4(3H)-one (4h)

(E)-2-(2,4-Dihydroxystyryl)-3-(4-ethynylphenyl)pyrido[2,3-d]pyrimidin-4(3H)-one (4i)

(E)-2-(2,5-Dihydroxystyryl)-3-(4-ethynylphenyl)pyrido[2,3-d]pyrimidin-4(3H)-one (4j)

(E)-3-(4-Ethynylphenyl)-2-(4-hydroxy-3-methoxystyryl)pyrido[2,3-d]pyrimidin-4(3H)-one (4k)

(E)-3-(4-Ethynylphenyl)-2-(4-hydroxy-3-nitrostyryl)pyrido[2,3-d]pyrimidin-4(3H)-one (4l)

(E)-2-(3,5-Dimethoxystyryl)-3-(4-ethynylphenyl)pyrido[2,3-d]pyrimidin-4(3H)-one (4m)

(E)-2-(2,5-Dimethoxystyryl)-3-(4-ethynylphenyl)pyrido[2,3-d]pyrimidin-4(3H)-one (4n)

(E)-2-(2-(Benzo[d][1,3]dioxol-4-yl)vinyl)-3-(4-ethynylphenyl)pyrido[2,3-d]pyrimidin-4(3H)-one (4o)

(E)-3-(4-Ethynylphenyl)-2-(4-hydroxy-3,5-dimethylstyryl)pyrido[2,3-d]pyrimidin-4(3H)-one (4p)

(E)-3-(4-Ethynylphenyl)-2-(3,4,5-trimethoxystyryl)pyrido[2,3-d]pyrimidin-4(3H)-one (4q)

(E)-3-(4-Ethynylphenyl)-2-(2,4,6-trimethoxystyryl)pyrido[2,3-d]pyrimidin-4(3H)-one (4r)

(E)-3-(4-Ethynylphenyl)-2-(2-(naphthalen-2-yl)vinyl)pyrido[2,3-d]pyrimidin-4(3H)-one (4s)

(E)-3-(4-Ethynylphenyl)-2-(2-(quinolin-2-yl)vinyl)pyrido[2,3-a]pyrimidin-4(3H)-one (4t)

(E)-2-(2-(1H-Indol-5-yl)vinyl)-3-(4-ethynylphenyl)pyrido[2,3-d]pyrimidin-4(3H)-one (4u)

(E)-3-(4-Ethynylphenyl)-2-(2-(5-methoxy-1H-indol-3-yl)vinyl)pyrido[2,3-d]pyrimidin-4(3H)-one (4v)

(E)-3-(4-Ethynylphenyl)-2-(2-(5-nitrofuran-2-yl)vinyl)pyrido[2,3-d]pyrimidin-4(3H)-one (4w)

(E)-3-(4-Ethynylphenyl)-2-(2-(5-nitrothiophen-2-yl)vinyl)pyrido[2,3-d]pyrimidin-4(3H)-one (4x)

In yet another embodiment of the present invention, the structural formulae of the representative compounds of formula A are:

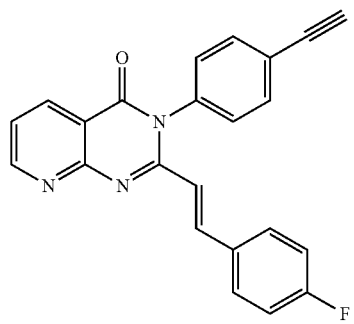

4a

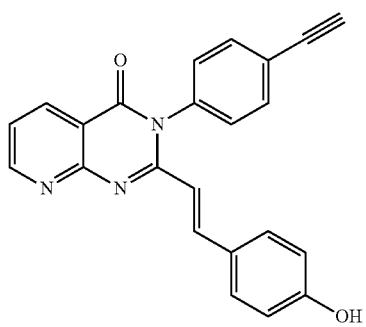

4b

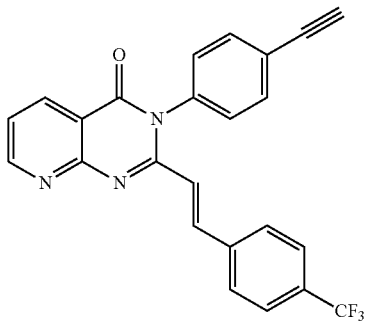

4c

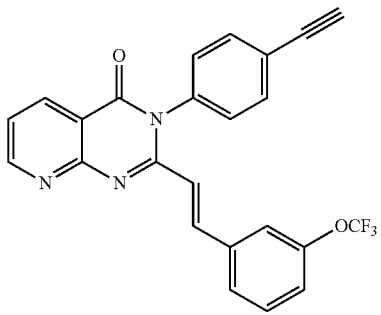

4d

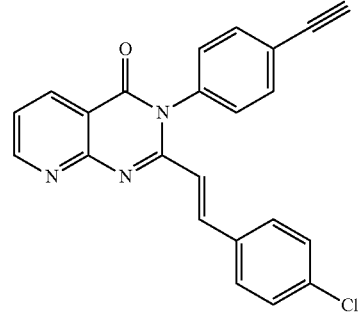

4e

-continued
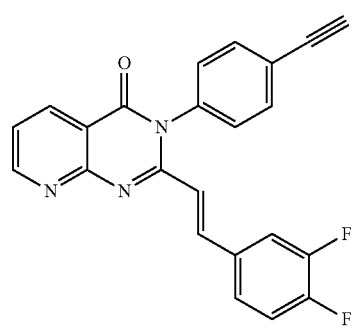
4f
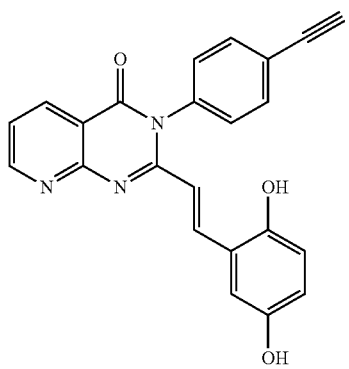
4g
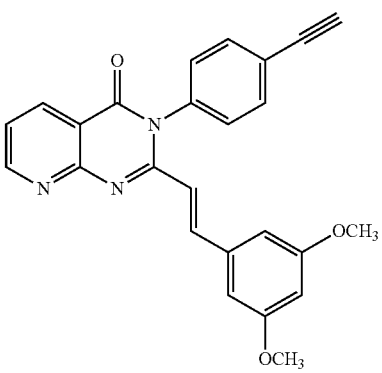
4h
4i
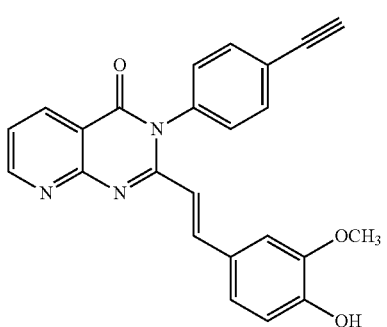
4j
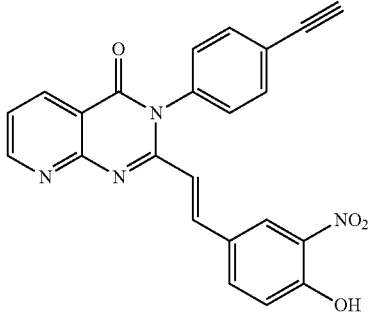
4k
4l
4m -continued
4n
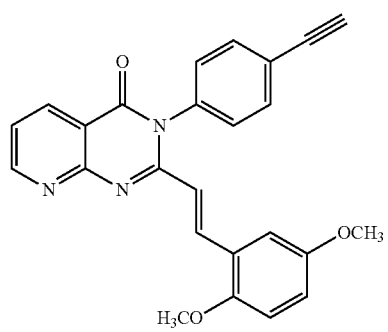
4o
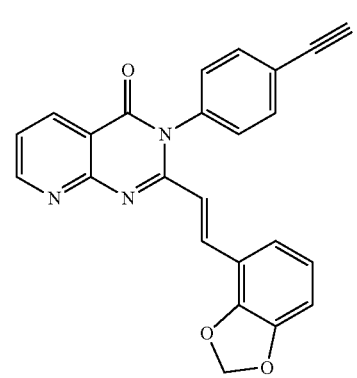
4p
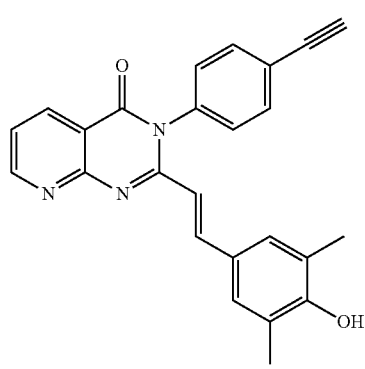
4q
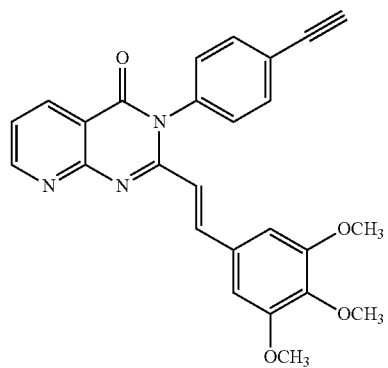
-continued
4r
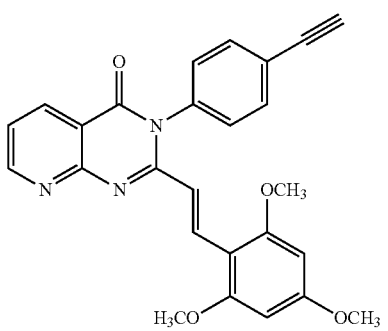
4s
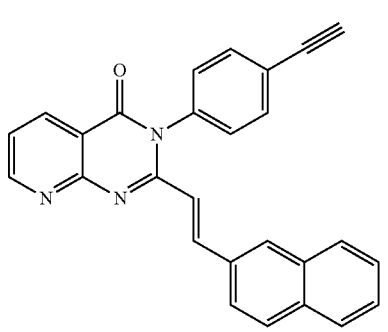
4t
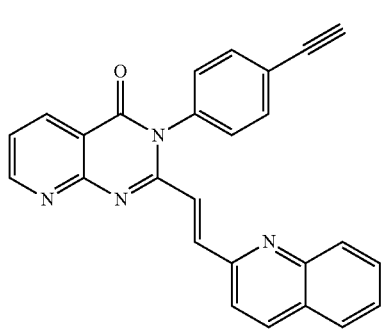
4u
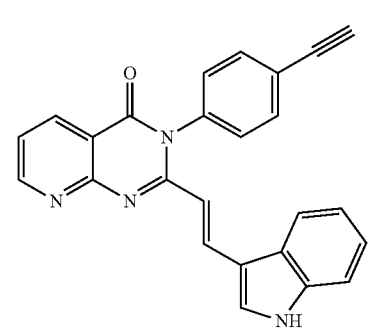
4v
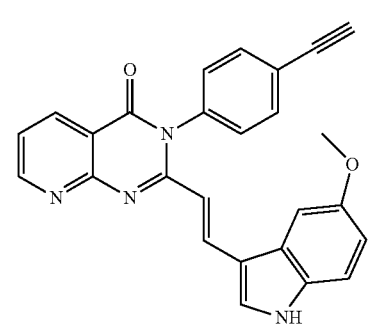

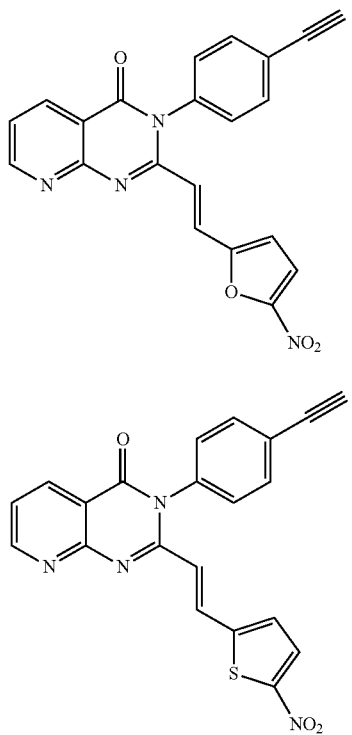

In yet another embodiment of the present invention, the representative compounds of formula A are useful as anti-cancer agents.

A compound of formula A of formula 4b, 4c, 4g, 4q, 4s and 4t, wherein said compounds exhibit an in vitro anticancer activity against human cancer cell lines selected from the group consisting of leukemia cell line, non small cell lung cell line, colon cell line, CNS cell line, renal cell line, prostate cell line, ovarian cell line, breast cell line, and melanoma cell line Accordingly, the present invention also provides a process for the preparation of compound of formula A comprising the steps of:

a: reacting 2-aminonicotinic acid with acetic anhydride at reflux temperature for a time period lying in the range of 10 to 45 minutes to obtain 2-methyl-4H-pyrido[2,3-d][1,3]oxazin-4-one (6),

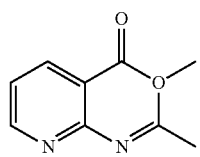

b. reacting 2-methyl-4H-pyrido[2,3-d][1,3]oxazin-4-one (6) obtained in step (a) with 4-ethynylaniline (7) in an organic solvent under reflux conditions for a time period lying in the range of 2 to 10 hours to obtain 2-methyl3-(4-ethynylphenyl)-2-methylpyrido[2,3-d]pyrimidin-4(3H)-one (8),

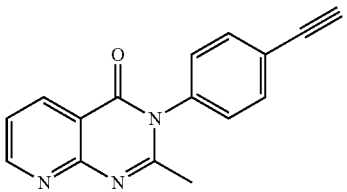

c. reacting 2-methyl3-(4-ethynylphenyl)-2-methylpyrido[2,3-d]pyrimidin-4(3H)-one (8) obtained in step (b) with substituted aldehydes in an organic solvent under reflux conditions for a time period lying in the range of 6 to 10 hours to obtain the desired products of formulae 4a-x.

In an embodiment of the invention wherein the organic solvent used in step (b) and (c) is selected from the group consisting of acetic acid, propionic acid, and DMF.

In another embodiment of the invention wherein the substituted aldehyde used in step (c) is selected from the group consisting of 3,4,5-trimethoxybenzaldehyde,2,4,6-trimethoxy benzaldehyde, 2,5-dimethoxybenzaldehyde, 3,5-dimethoxybenzaldehyde, quinoline-2-carboxaldehyde, 2-naphthaldehyde, 4-fluorobenzaldehyde, 3,4-difluoro benzaldehyde, 4-hydroxybenzaldehyde, indole-5-carboxaldehyde, 5-methoxy-indole-3-carboxaldehyde, 3-methoxy-4-hydroxybenzaldehyde, piperonal, 3-fluoro-4-methoxy benzaldehyde, 3-fluoro-4-chlorobenzadehyde, 4-trifluoromethylbenzaldehyde, 3-trifluoromethoxybenzaldehyde, 4-chlorobenzaldehyde, 2,4-dihydroxy benzaldehyde, and 2,5-dihydroxybenzaldehyde.

In one more another embodiment of the invention wherein the reflux temperature in step (a) lies in the range of 150-155° C.

In yet another embodiment of the invention wherein the reflux temperature in step (b) and (c) lies in the range of 120-125° C.

In still another embodiment of the invention wherein the yield of obtaining the products of formulae 4a-x lies in the range of 85-90%.

BRIEF DESCRIPTION OF ACCOMPANYING DRAWINGS

FIG. 1 represents the structures of substituted aldehydes.

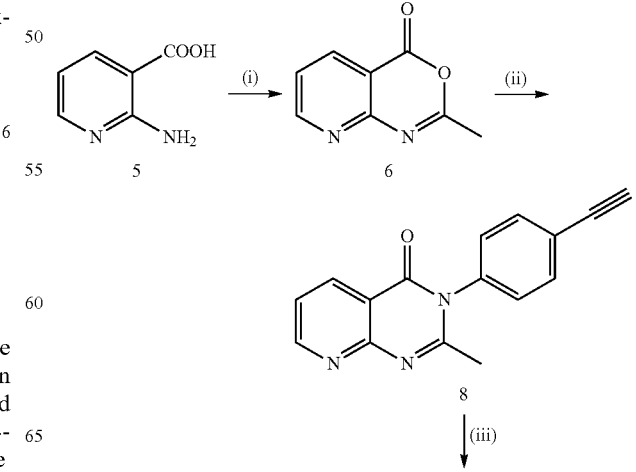

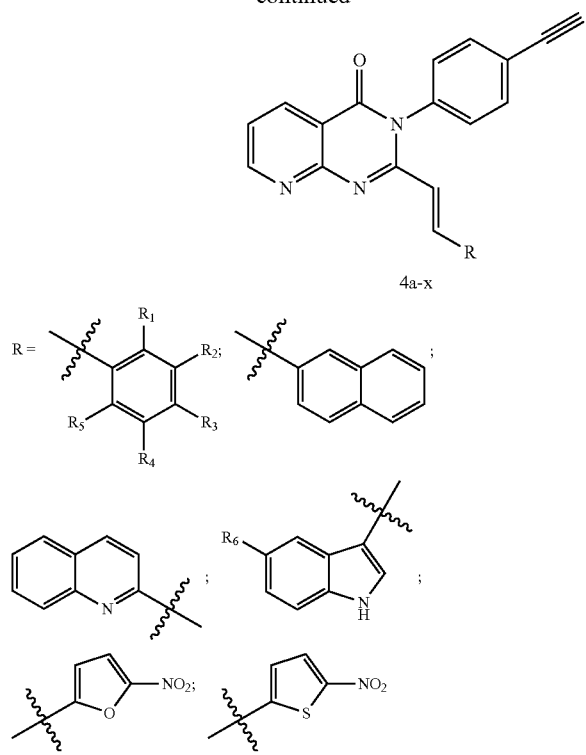

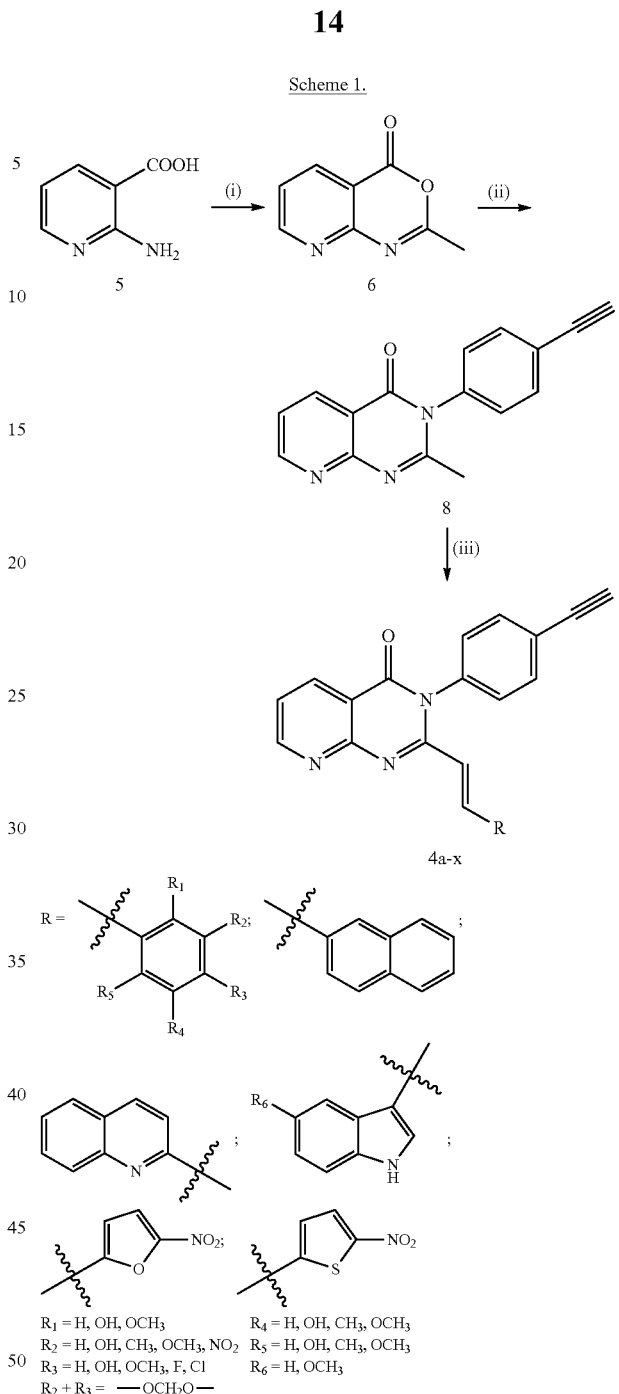

Scheme 1.

Reagents and conditions: (i) Ac₂O, 150-155° C., 30-45 min; (ii) 4-ethynylaniline (7), AcOH, reflux, 8-10 h (iv) Substituted aldehydes, AcOH, reflux, 8-10 h.

FIG. 2 (Scheme 1) represents the flow diagram for the preparation of compound of formula A wherein reagent and conditions are: (i) Ac₂O, 150-155° C., 10-45 min; (ii) 4-ethynylaniline (7), AcOH, reflux, 6-10 h (iv) Substituted aldehydes, AcOH, reflux, 8-10 h.

DETAILED DESCRIPTION OF THE INVENTION 3-(4-ethynylphenyl)pyridopyrimidinone compounds have shown promising anticancer activity in various cell lines. The molecules synthesized are of immense biological significance. This resulted in design and synthesis of new congeners as illustrated in FIG. 2 (Scheme-1), which comprise:

i. Cyclization of 2-aminonicotinic acid (5) on reaction with acetic anhydride at 150-155° C. for 30-45 min.

ii. Insertion reaction of 2-methyl-4H-pyrido[2,3-d][1,3] oxazin-4-one (6) and 4-ethynylaniline (7a-d) in acetic acid under reflux conditions afforded 3-(4-ethynylphenyl)-2-methylpyrido[2,3-d]pyrimidin-4(3H)-one (8a-d).

iii. The synthesis of 3-(4-ethynylphenyl)pyridopyrimidinone compounds (4a-x) as potential anticancer agents were synthesized by the reaction of 3-(4-ethynylphenyl)-2-methylpyrido[2,3-d]pyrimidin-4(3H)-one (8a-d) with different aldehydes in acetic acid under reflux to give the final compounds. Purification by column chromatography using different solvents like ethyl acetate, hexane, chloroform and methanol.

The 3-(4-ethynylphenyl)pyridopyrimidinone compounds exhibited significant anticancer activity against sixty human cancer cell lines.

3-(4-ethynylphenyl)pyridopyrimidinone compounds of formula 4b, 4c, 4g, 4q, 4s and 4t exhibiting an in vitro anticancer activity against sixty human cancer cell lines derived from nine cancer types leukemia cell line, non small cell lung cell line, colon cell line, CNS cell line, renal cell line, prostate cell line, ovarian cell line, breast and melanoma cell line.

3-(4-ethynylphenyl)pyridopyrimidinone compounds of formula 4b, 4c, 4g, 4q, 4s and 4t exhibiting an in vitro anticancer activity against six leukemia cancer cell lines (CCRF-CEM, HL-60, K-562, MOLT-4, SR and RPMI-8226) for $GI_{50}$ are in the range of 3.58 to 5.55, 0.45 to 2.43, 0.25 to 0.54 and 1.39 to 3.01, 0.26 to 0.45, 3.20 to 7.35 □M, respectively at an exposure period of at least 48 h.

3-(4-ethynylphenyl)pyridopyrimidinone compounds of formula 4b, 4c, 4g, 4q, 4s and 4t exhibiting an in vitro anticancer activity against nine non-small cell lung cancer cell lines (A549/ATCC, EKVX, HOP-62, HOP-92, NCI-H226, NCI-H23, NCI-H322M, NCI-H460 and NCI-H522) for $GI_{50}$ are in the range of 2.31 to 17.3, 1.63 to 7.45, 0.20 to 0.58 and 1.32 to 3.90, 0.18 to 0.70, 1.80 to 5.66 DM, respectively at an exposure period of at least 48 h.

3-(4-ethynylphenyl)pyridopyrimidinone compounds of formula 4b, 4c, 4g, 4q, 4s and 4t exhibiting an in vitro anticancer activity against seven colon cancer cell line (COLO 205, HCC-2998, HCT-116, HCT-15, HT29, KM12 and SW-620) for $GI_{50}$ are in the range of 3.19 to 27.5, 2.06 to 3.26, 0.33 to 0.37 and 1.64 to 2.23, 0.30 to 0.36, 3.55 to 52.8 DM, respectively at an exposure period of at least 48 h.

3-(4-ethynylphenyl)pyridopyrimidinone compounds of formula 4b, 4c, 4g, 4q, 4s and 4t exhibiting an in vitro anticancer activity against six CNS cancer cell line (SF-268, SF-295, SF-539, SNB-19, SNB-75 and U251) for $GI_{50}$ are in the range of 3.88 to 16.2, 2.60 to 3.69, 0.34, 1.67 to 2.27, 0.20 to 0.72, 0.94 to 5.24 □M, respectively at an exposure period of at least 48 h.

3-(4-ethynylphenyl)pyridopyrimidinone compounds of formula 4b, 4c, 4g, 4q, 4s and 4t exhibiting an in vitro anticancer activity against nine melanoma cancer cell line (LOX IMVI, MALME-3M, M14, MDA-MB-435, SK-MEL-2, SK-MEL-28, SK-MEL-5, UACC-257 and UACC-62) for $GI_{50}$ are in the range of 1.78 to 34.6, 0.51 to 4.97, 0.19 to 0.54 and 1.49 to 2.27, 0.19 to 1.21, 1.60 to 6.30 □M, respectively at an exposure period of at least 48 h.

3-(4-ethynylphenyl)pyridopyrimidinone compounds of formula 4b, 4c, 4g, 4q, 4s and 4t exhibiting an in vitro anticancer activity against seven ovarian cancer cell lines (IGROV1, OVCAR-3, OVCAR-4, OVCAR-5, OVCAR-8, NCI/ADR-RES and SK-OV-3) for $GI_{50}$ are in the range of 2.33 to 9.67, 1.95 to 7.55, 0.30 to 0.48 and 1.67 to 3.61, 0.30 to 0.40, 2.41 to 32.3 □M respectively at an exposure period of at least 48 h.

3-(4-ethynylphenyl)pyridopyrimidinone compounds of formula 4b, 4c, 4g, 4q, 4s and 4t said compounds exhibiting an in vitro anticancer activity against eight renal cancer cell line (786-0, A498, ACHN, CAKI-1, SN12C, TK-10, UO-31 and RXF 393) for are in the range of 2.63 to 20.5, 1.69 to 4.08, 0.28 to 0.36, 1.43 to 2.34, 0.22 to 0.43, 1.48 to 8.78 □M, respectively at an exposure period of at least 48 h.

3-(4-ethynylphenyl)pyridopyrimidinone compounds of formula 4b, 4c, 4g, 4q, 4s and 4t exhibiting an in vitro anticancer activity against two prostate cancer cell line (PC-3, DU-145) for $GI_{50}$ are 3.96 to 5.36, 2.35 to 7.45, 0.34, 1.96 to 3.76, 0.28 to 0.34, 3.87 to 4.10 □M, respectively at an exposure period of at least 48 h.

3-(4-ethynylphenyl)pyridopyrimidinone compounds of formula 4b, 4c, 4g, 4q, 4s and 4t exhibiting an in vitro anticancer activity against six breast cancer cell line (MCF-7, MDA-MB-231/ATCC, HS 578T, TD-47D, MDA-MB-468 and BT-549) for $GI_{50}$ are in the range of 2.83 to 5.85, 0.96 to 7.62, 0.24 to 0.41, 1.51 to 3.46, 0.23 to 0.35, 2.31 to 11.4 □M, respectively at an exposure period of at least 48 h.

In the present study, we investigated the antiproliferative activity of a series of 17 pyridopyrimidines. We found that compound 4g showed a good profile at nanomolar range growth inhibition activity in several cancer cell lines. These findings indicate that compound 4g is a promising candidate as a novel antitumor agent.

EXAMPLES

The following examples are given by way of illustration of the present invention and therefore should not be construed to limit the scope of the present invention.

Example 1

(E)-3-(4-Ethynylphenyl)-2-(4-fluorostyryl)pyrido[2,3-d]pyrimidin-4(3H)-one (4a)

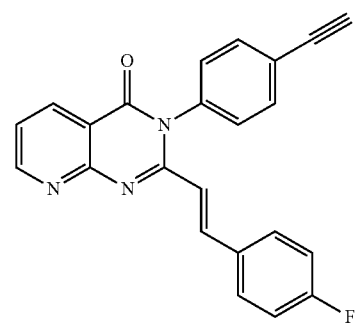

4a

2-Aminonicotinic acid (1.6 g, 10 mmol) was dissolved in acetic anhydride (10 ml), resulting mixture refluxed for 15 min, after completion of the reaction water was added, quenched with $NaHCO_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of $NaHCO_3$ solution. Reaction mixture extracted with ethyl acetate, combined organic layer dried under vacuum, crude mass purified by column chromatography by using (7:3) hexane, ethyl acetate as eluent to afford compound 2-methyl3-(4-ethynylphenyl)-2-methyl-pyrido[2,3-d]pyrimidin-4(3H)-one as a white solid. This compound (275 mg, 1 mmol) was dissolved in acetic acid, to this 4-fluorobenzaldehyde (123 mg, 1 mmol) was added, resulting mixture was stirred at reflux for 6 h and poured into ice water. The mixture was neutralized by the addition of $NaHCO_3$ solution. Reaction mixture extracted with ethyl acetate, combined organic layer dried under vacuum, crude mass purified by column chromatography by using (7:3) hexane, ethyl acetate as eluent to afford compound 4a as light yellow solid.

Yield: 85%. Mp 123-124° C.; $^1$H NMR (300 MHz, $CDCl_3$) δ 3.25 (s, 1H), 6.35 (d, 1H, J=15.1 Hz), 7.07 (m, 2H), 7.32 (t, 2H, J=14.3 Hz), 7.36 (d, 1H, J=7.5 Hz), 7.44 (m, 2H), 7.73 (d, 2H, J=8.3 Hz), 8.22 (d, 1H, J=15.1 Hz), 8.60 (m, 1H), 9.03 (m, 1H); LRMS (ESI, m/z) 368 ($M^+$).

Example 2

(E)-3-(4-Ethynylphenyl)-2-(4-hydroxystyryl)pyrido[2,3-d]pyrimidin-4(3H)-one (4b)

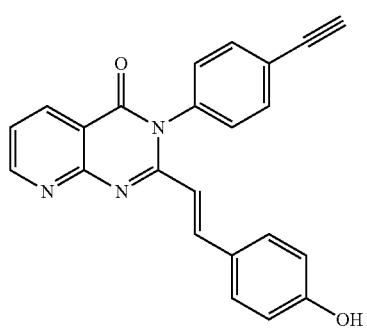

2-Aminonicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 2-methyl-3-(4-ethynylphenyl)-2-methyl-pyrido[2,3-d]pyrimidin-4(3H)-one as white solid. This compound (275 mg, 1mmol) was dissolved in acetic acid, to this 4-hydroxybenzaldehyde (122 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4b as light yellow solid.

Yield: 85%. Mp 122-123° C.; $^1$H NMR (300 MHz, CDCl$_3$) δ 1.61 (s, 1H), 3.25 (s, 1H), 6.35 (d, 1H, J=15.1 Hz), 7.07 (m, 2H), 7.32 (t, 2H, J=14.3 Hz), 7.36 (d, 1H, J=7.5 Hz), 7.44 (m, 2H), 7.73 (d, 2H, J=8.3 Hz), 8.22 (d, 1H, J=15.1 Hz), 8.61 (m, 1H), 9.03 (m, 1H); LRMS (ESI, m/z) 366 (M$^+$).

Example 3

(E)-3-(4-Ethynylphenyl)-2-(4-(trifluoromethyl)styryl)pyrido[2,3-d]pyrimidin-4(3H)-one (4c)

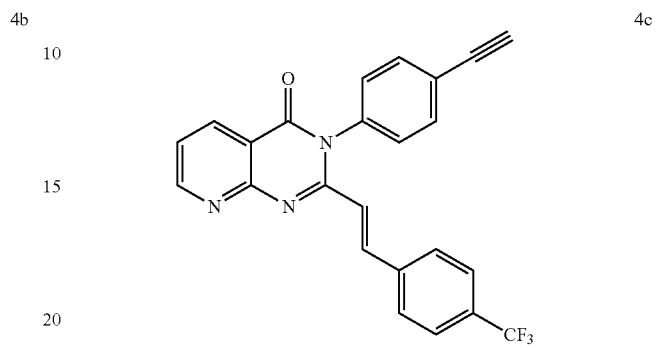

2-Aminonicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 2-methyl3-(4-ethynylphenyl)-2-methyl-pyrido[2,3-d]pyrimidin-4(3H)-one as white solid. This compound (275 mg, 1 mmol) was dissolved in acetic acid, to this 4-trifluoromethylbenzaldehyde (174 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4c as light yellow solid.

Yield 86%. Mp 127-128° C.; $^1$H NMR (300 MHz, CDCl$_3$) δ 3.254 (s, 1H), 6.35 (d, 1H, J=15.1 Hz), 7.07 (m, 2H), 7.31 (t, 2H, J=14.3 Hz), 7.36 (d, 1H, J=7.5 Hz), 7.44 (m, 2H), 7.73 (d, 2H, J=8.3 Hz), 8.22 (d, 1H, J=15.1 Hz), 8.61 (m, 1H), 9.03 (m, 1H); LRMS (ESI, m/z) 418 (M$^+$).

Example 4

(E)-3-(4-Ethynylphenyl)-2-(3-(trifluoromethoxy)styryl)pyrido[2,3-d]pyrimidin-4(3H)-one (4d)

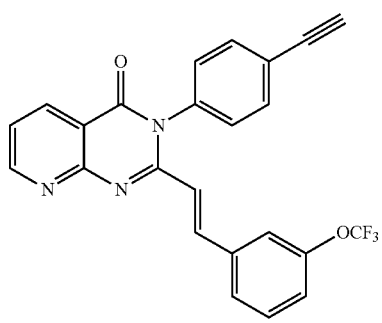

4d

2-Amino nicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this 3-trifluoromethoxy benzaldehyde (190 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4d as light yellow solid.

Yield 87%.; Mp128-129° C.; $^1$H NMR (300 MHz, CDCl$_3$) δ 3.25 (s, 1H), 6.35 (d, 1H, J=15.1 Hz), 7.07 (m, 2H), 7.32 (t, 2H, J=8.3 Hz, J=14.3 Hz), 7.36 (d, 1H, J=7.5 Hz), 7.44 (m, 2H), 7.73 (d, 2H, J=8.3 Hz), 8.22 (d, 1H, J=15.1 Hz), 8.60 (m, 1H), 9.03 (m, 1H); LRMS (ESI, m/z) 434 (M$^+$).

Example 5

(E)-2-(3,4-Difluorostyryl)-3-(4-ethynylphenyl)pyrido[2,3-d]pyrimidin-4(3H)-one (4t)

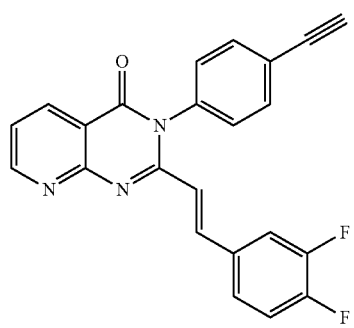

4f

2-Aminonicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 2-methyl3-(4-ethynylphenyl)-2-methyl-pyrido[2,3-d]pyrimidin-4(3H)-one as white solid. This compound (275 mg, 1 mmol) was dissolved in acetic acid, to this 3,4-difluorobenzaldehyde (142 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4f as light yellow solid.

Yield: 85%. Mp 123-124° C.; $^1$H NMR (300 MHz, CDCl$_3$) δ 3.25 (s, 1H), 6.36 (d, 1H, J=15.1 Hz), 7.07 (m, 2H), 7.32 (t, 2H, J=14.3 Hz), 7.36 (d, 1H, J=7.5 Hz), 7.44 (m, 1H), 7.73 (d, 2H, J=8.31 Hz), 8.22 (d, 1H, J=15.1 Hz), 8.6 (m, 1H), 9.03 (m, 1H) LRMS(ESI, m/z) 386 (M$^+$).

Example 6

(E)-2-(4-chloro-3-fluorostyryl)-3-(4-ethynylphenyl)pyrido[2,3-d]pyrimidin-4(3H)-one (4g)

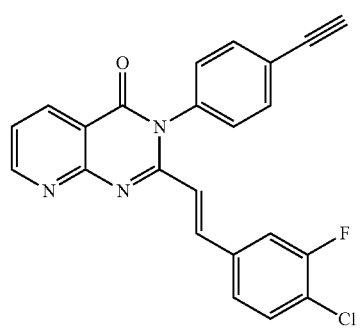

4g

2-Aminonicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this 3-fluoro-4-chloro benzaldehyde (158 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4g as light yellow solid.

Yield 90%.; Mp 126-127° C.; $^1$H NMR (300 MHz, CDCl$_3$) δ 3.25 (s, 1H), 6.35 (d, 1H, J=15.1 Hz), 7.07 (m, 2H), 7.32 (t, 2H, J=14.3 Hz), 7.36 (d, 1H, J=7.5 Hz), 7.44 (m, 1H), 7.73 (d, 2H, J=8.3 Hz), 8.22 (d, 1H, J=15.1 Hz), 8.60 (m, 1H), 9.03 (m, 1H); LRMS (ESI, m/z) 402 (M$^+$).

Example 7

(E)-3-(4-Ethynylphenyl)-2-(3-fluoro-4-methoxystyryl)pyrido[2,3-d]pyrimidin-4(3H)-one (4h)

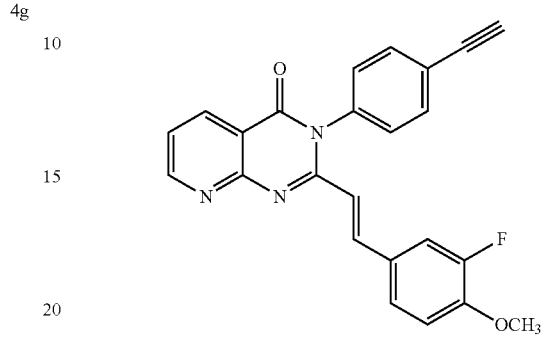

4h

2-Amino nicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this 3-fluoro-4-methoxy benzaldehyde (154 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4h as light yellow solid.

Yield 90%.; Mp124-125° C.; $^1$H NMR (300 MHz, CDCl$_3$) δ 3.25 (s, 1H), 3.90 (s, 3H), 6.35 (d, 1H, J=15.1 Hz), 7.07 (m, 2H), 7.32 (t, 2H, J=14.3 Hz), 7.36 (d, 1H, J=7.5 Hz), 7.44 (m, 1H), 7.73 (d, 2H, J=8.3 Hz), 8.22 (d, 1H, J=15.1 Hz), 8.60 (m, 1H), 9.03 (m, 1H); LRMS (ESI, m/z) 398 (M$^+$).

Example 8

(E)-3-(4-Ethynylphenyl)-2-(4-hydroxy-3-methoxystyryl)pyrido[2,3-d]pyrimidin-4(3H)-one (4k)

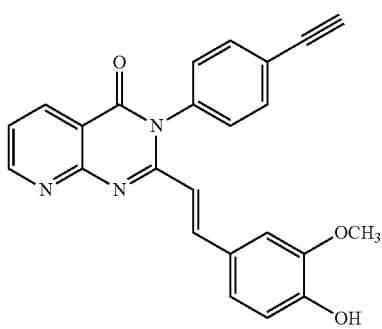

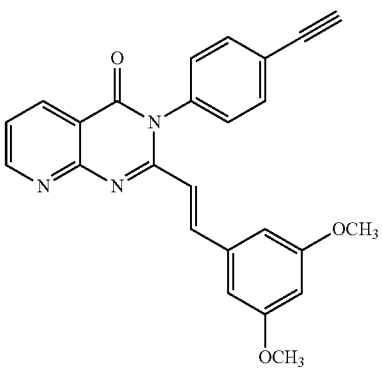

2-Amino nicotinic acid (1.6 g, 10 mmol) was dissolved in acetic anhydride (10 ml), resulting mixture refluxed for 15 min, after completion of the reaction water was added, quenched with NaHCO₃ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this 3-methoxy-4-hydroxy benzaldehyde (152 mg, 1mmol) was added, resulting mixture was stirred at reflux for 6 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 4k as light yellow solid.

Yield 85%; Mp123-124° C.; $^1$H NMR (300 MHz, CDCl₃) δ 3.25 (s, 1H), 3.90 (s, 3H), 6.35 (d, 1H, J=15.1 Hz), 7.07 (m, 2H), 7.32 (t, 2H, J=14.3 Hz), 7.36 (d, 1H, J=7.55 Hz), 7.44 (m, 1H), 7.73 (d, 2H, J=8.309 Hz), 8.22 (d, 1H, J=15.1 Hz), 8.60 (m, 1H), 9.03 (m, 1H), 9.83 (s, 1H); LRMS (ESI, m/z) 396 (M⁺).

Example 9

(E)-2-(3,5-Dimethoxystyryl)-3-(4-ethynylphenyl)pyrido[2,3-d]pyrimidin-4(3H)-one (4m)

2-Amino nicotinic acid (1.6 g, 10 mmol) was dissolved in acetic anhydride (10 ml), resulting mixture refluxed for 15 min, after completion of the reaction water was added, quenched with NaHCO₃ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this 3,5-dimethoxybenzaldehyde (165 mg, 1 mmol) was added, resulting mixture was stirred at reflux for 6 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 4m as light yellow solid.

Yield 87%; Mp123-124° C.; $^1$H NMR (300 MHz, CDCl₃) δ 3.59 (s, 1H) 3.74 (s, 6H), 6.69 (d, 1H, J=15.4 Hz), 6.77 (d, 1H), 6.85 (s, 1H), 7.06 (d, 1H, J=8.3 Hz), 7.30 (t, 2H, J=17.5 Hz), 7.41 (m, 1H), 7.54 (d, 1H, J=13.4 Hz), 7.71 (d, 2H, J=8.12 Hz), 8.38 (d, 1H, J=15.2 Hz), 8.59 (d, 1H, J=7.9 Hz); LRMS (ESI, m/z) 410 (M⁺).

Example 10

(E)-2-(2,5-Dimethoxystyryl)-3-(4-ethynylphenyl)pyrido[2,3-d]pyrimidin-4(3H)-one (4n)

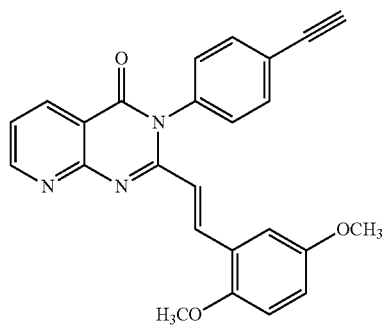

2-Amino nicotinic acid (1.6 g, 10 mmol) was dissolved in acetic anhydride (10 ml), resulting mixture refluxed for 15 min, after completion of the reaction water was added, quenched with NaHCO₃ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 2-methyl3-(4-ethynylphenyl)-2-methyl-pyrido[2,3-d]pyrimidin-4(3H)-one as white solid. This compound275 mg, 1 mmol) was dissolved in acetic acid, to this 2,5-dimethoxy benzaldehyde (165 mg, 1 mmol) was added, resulting mixture was stirred at reflux for 6 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 4n as light yellow solid.

Yield 90%; Mp 127-128° C.; $^1$H NMR (300 MHz, CDCl₃) δ 3.59 (s, 1H), 3.74 (s, 6H), 6.69 (d, 1H, J=15.4 Hz), 6.77 (d, 1H), 6.85 (s, 1H), 7.06 (d, 1H, J=8.3 Hz), 7.30 (t, 2H, J=8.31, J=17.5 Hz), 7.41 (m, 1H), 7.54 (d, 1H, J=13.4 Hz), 7.71 (d, 2H, J=8.12 Hz), 8.38 (d, 1H, J=15.2 Hz), 8.595 (d, 1H, J=7.9 Hz); LRMS (ESI, m/z) 410 (M⁺).

Example 11

(E)-2-(2-(benzo[d][1,3]dioxol-4-yl)vinyl)-3-(4-ethynylphenyl)pyrido[2,3-d]pyrimidin-4(3H)-one (4o)

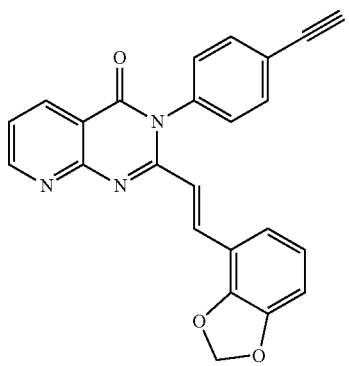

2-Amino nicotinic acid (1.6 g, 10 mmol) was dissolved in acetic anhydride (10 ml), resulting mixture refluxed for 15 min, after completion of the reaction water was added, quenched with NaHCO₃ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 2-methyl3-(4-ethynylphenyl)-2-methyl-pyrido[2,3-d]pyrimidin-4(3H)-one as white solid. This compound (275 mg, 1 mmol) was dissolved in acetic acid, to this piperonal (148 mg, 1 mmol) was added, resulting mixture was stirred at reflux for 6 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 4o as light yellow solid.

Yield 85%; Mp 125-126° C.; $^1$H NMR (300 MHz, CDCl₃) δ 3.69 (s, 1H), 3.20 (s, 1H), 6.77 (t, 1H), 6.93 (d, 1H, J=15.8 Hz), 7.07 (s, 1H), 7.29 (s, 1H), 7.39 (d, 2H, J=7.5 Hz), 7.57 (s, 1H), 7.72 (d, 2H, J=8.3 Hz), 8.24 (d, 1H, J=14.3 Hz), 8.58 (d, 1H, J=9.06 Hz), 9.00 (s, 1H); LRMS (ESL m/z) 394 (M⁺).

Example 12

(E)-3-(4-Ethynylphenyl)-2-(3,4,5-trimethoxystyryl)pyrido[2,3-d]pyrimidin-4(3H)-one (4q)

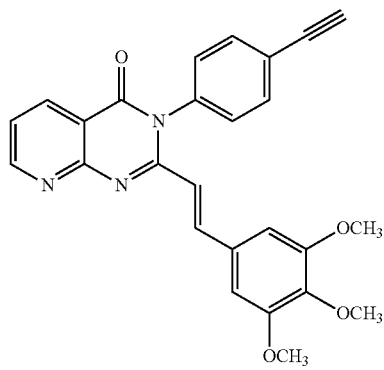

2-Aminonicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield the desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 2-methyl3-(4-ethynylphenyl)-2-methylpyrido[2,3-d]pyrimidin-4(3H)-one as white solid. This compound (275 mg, 1 mmol) was dissolved in acetic acid, to this 3,4,5-trimethoxybenzaldehyde (196 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4q as light yellow solid.

Yield 85%; Mp 123-124° C.; $^1$H NMR (300 MHz, CDCl$_3$) δ 3.69 (s, 1H), 3.81 (s, 9H), 6.22 (d, 1H, J=15.8 Hz), 6.57 (s, 1H), 7.27 (s, 1H), 7.31 (d, 2H, J=7.5 Hz), 7.43 (s, 1H), 7.73 (d, 2H, J=8.3 Hz), 8.23 (d, 1H, J=14.35 Hz), 8.628 (d, 1H, J=9.0 Hz), 9.03 (s, 1H); LRMS (ESI, m/z) 440 (M$^+$).

Example 13

(E)-3-(4-Ethynylphenyl)-2-(2,4,6-trimethoxystyryl)pyrido[2,3-d]pyrimidin-4(3H)-one (4r)

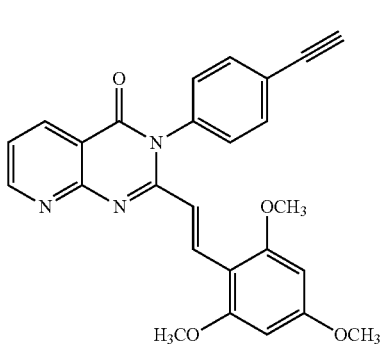

2-Amino nicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline 1.34 mg, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methylpyrido[2,3-d]pyrimidin-4(3H)-one as white solid. (1.61g, 1 mmol) was dissolved in acetic acid, to this 2,4,6-trimethoxybenzaldehyde 71.15 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford afford compound 4r as light yellow solid.

Yield 88%; Mp 124-125° C.; $^1$H NMR (300 MHz, CDCl$_3$) δ 3.69 (s, 1H) 3.81 (s, 9H), 6.22 (d, 1H, J=15.8 Hz), 6.57 (s, 1H), 7.27 (s, 1H), 7.31 (d, 2H, J=7.5 Hz), 7.43 (s, 1H), 7.73 (d, 2H, J=8.3 Hz), 8.23 (d, 1H, J=14.3 Hz), 8.63 (d, 1H, J=9.0 Hz), 9.03 (s, 1H) LRMS(ESI, m/z) 440 (M$^+$).

Example 14

(E)-3-(4-Ethynylphenyl)-2-(2-(naphthalen-2-yl)vinyl)pyrido[2,3-d]pyrimidin-4(3H)-one (4s)

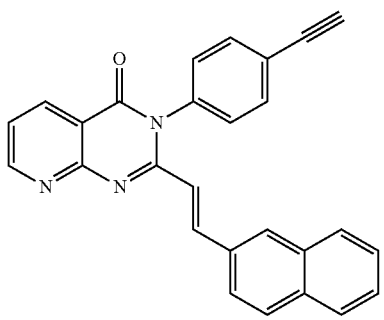

2-Amino nicotinic acid (1.6 g, 10 mmol) was dissolved in acetic anhydride (10 ml), resulting mixture refluxed for 15 min, after completion of the reaction water was added, quenched with NaHCO₃ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this 2-naphthaldehyde (154 mg, 1mmol) was added, resulting mixture was stirred at reflux for 6 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 4s as light yellow solid.

Yield 90%; Mp 129-130° C.; $^1$H NMR (300 MHz, CDCl$_3$) δ 3.26 (s, 1H), 6.49 (d, 1H, J=15.4 Hz), 7.36 (d, 3H, J=8.3 Hz), 7.44 (m, 1H), 7.51 (m, 2H), 7.78 (t, 4H, J=16.2 Hz), 7.87 (s, 2H), 8.48 (d, 1H, J=15.4 Hz), 8.61 (m, 1H), 9.04 (m, 1H; LRMS (ESI, m/z) 400(M$^+$).

Example 15

(E)-3-(4-Ethynylphenyl)-2-(2-(quinolin-2-yl)vinyl)pyrido[2,3-d]pyrimidin-4(3H)-one (4t)

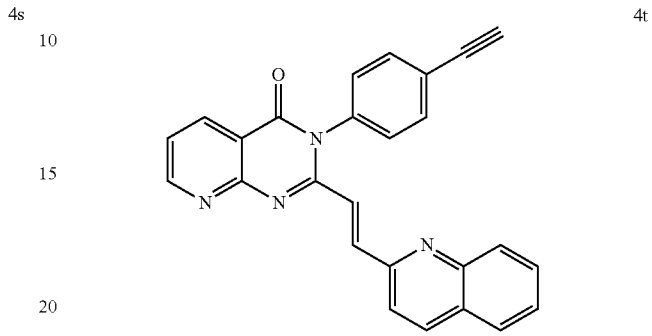

2-Amino nicotinic acid (1.6 g, 10 mmol) was dissolved in acetic anhydride (10 ml), resulting mixture refluxed for 15 min, after completion of the reaction water was added, quenched with NaHCO₃ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this quinoline-2-carboxaldehyde (157 mg, 1 mmol) was added, resulting mixture was stirred at reflux for 6 h and poured into ice water. The mixture was neutralized by the addition of NaHCO₃ solution. Reaction mixture extracted with ethyl acetate, combined organic layer dried under vacuum, crude mass purified by column chromatography by using (7:3) hexane, ethyl acetate as eluent to afford compound 4t as light yellow solid.

Yield 88%; Mp 129-130° C.; $^1$H NMR (300 MHz, CDCl$_3$) δ 3.25 (s, 1H), 6.49 (d, 1H, J=15.4 Hz), 7.36 (d, 3H, J=8.3 Hz), 7.44 (m, 1H), 7.51 (m, 2H), 7.78 (t, 3H, J=8.4 Hz, J=16.2 Hz), 7.87 (s, 2H), 8.48 (d, 1H, J=15.4 Hz), 8.61 (m, 1H), 9.04 (m, 1H); LRMS (ESI, m/z) 401 (M$^+$)

Example 16

(E)-2-(2-(1H-Indol-5-yl)vinyl)-3-(4-ethynylphenyl)pyrido[2,3-d]pyrimidin-4(3H)-one (4u)

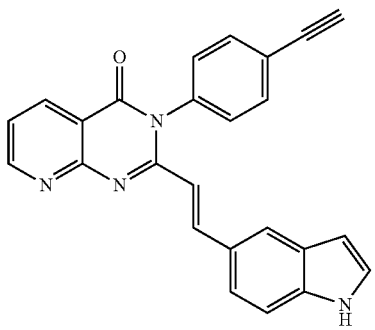

2-Amino nicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound2-methyl3-(4-ethynylphenyl)-2-methyl-pyrido[2,3-d]pyrimidin-4(3H)-one as white solid. This compound (275 mg, 1 mmol) was dissolved in acetic acid, to this indole-5-carboxaldehyde (145 mg, 1mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4u as light yellow solid.

Yield 90%; Mp 123-124° C.; $^1$H NMR (300 MHz, CDCl$_3$) δ 3.20 (t, 2H), 3.25 (s, 1H), 3.50 (t, 2H), 6.35 (d, 1H, J=15.1 Hz), 7.07 (m, 2H), 7.32 (t, 2H, J=8.3 Hz, J=14.3 Hz), 7.36 (d, 1H, J=7.5 Hz), 7.44 (m, 2H), 7.73 (d, 1H, J=8.3 Hz), 8.22 (d, 1H, J=15.1 Hz), 8.60 (m, 1H), 9.03 (m, 1H); LRMS (ESI, m/z) 389 (M$^+$).

Example 17

(E)-3-(4-ethynylphenyl)-2-(2-(5-methoxy-1H-indol-3-yl)vinyl)pyrido[2,3-d]pyrimidin-4(3H)-one (4v)

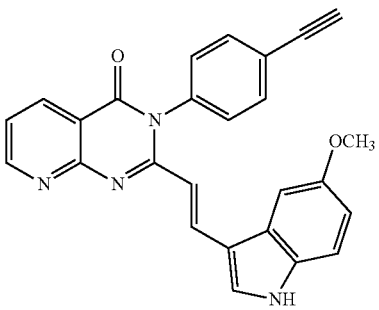

2-Amino nicotinic acid (1.6 g, 10 mmol) was dissolved in acetic anhydride (10 ml), resulting mixture refluxed for 15 min, after completion of the reaction water was added, quenched with NaHCO$_3$ solution, resulting reaction mixture extracted with ethyl acetate. Organic layer concentrated under vacuum to yield desired product 2-methyl-4H-pyrido[2,3-d][1,3]oxazin-4-one. The resulted compound (1.6 g, 1 mmol) was dissolved in acetic acid, to this 4-ethynylaniline (1.34 g, 1 mmol) was added, resulting mixture was stirred at reflux for 2 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 2-methyl3-(4-ethynylphenyl)-2-methyl-pyrido[2,3-d]pyrimidin-4(3H)-one as white solid. This compound (275 mg, 1 mmol) was dissolved in acetic acid, to this 5-methoxy-indole-3-carboxaldehyde 175 mg, 1 mmol) was added, resulting mixture was stirred at reflux for 6 h and poured into ice water. The mixture was neutralized by the addition of NaHCO$_3$ solution. Reaction mixture extracted with ethyl acetate, combined organic layer dried under vacuum, crude mass purified by column chromatography by using (7:3) hexane, ethyl acetate as eluent to afford compound 4v as light yellow solid.

Yield 88%; Mp114-115° C.; $^1$H NMR (300 MHz, CDCl$_3$) δ 3.20 (t, 2H), 3.25 (s, 1H), 3.50 (t, 2H), 3.90 (s, 3H), 6.35 (d, 1H, J=15.1 Hz), 7.07 (m, 2H), 7.32 (t, 2H, J=8.3 Hz, J=14.3 Hz), 7.36 (d, 1H, J=7.5 Hz), 7.44 (m, 2H), 7.73 (d, 1H, J=8.3 Hz), 8.22 (d, 1H, J=15.1 Hz), 8.60 (m, 1H), 9.03 (m, 1H); LRMS (ESI, m/z) 419 (M$^+$).

Biological Activity

Some of biological activity studies were carried out at the National Cancer Institute (NCI), Maryland, USA.

Anticancer Activity:

The compounds were evaluated for anticancer activity against sixty human cancer cells derived from nine cancer types (leukemia cell line, non-small-cell lung cell line, colon cell line, CNS cell line, melanoma cell line, ovarian cell line, prostate cell line, renal cell line and breast cancer cell line) as shown in Table 1. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth.

TABLE 1

The GI$_{50}$ (the concentration needed to reduce the growth of treated cells to half that of untreated cells) values for compounds 4b, 4c, 4g, 4q, 4s and 4t in sixty cancer cell lines.

| | Growth Inhibition GI$_{50}$ (μM) | | | | | |
|---|---|---|---|---|---|---|
| Panel/ Cell line | NSC766334 4b | NSC766326 4c | NSC766320 4g | NSC766314 4q | NSC766317 4s | NSC766329 4t |
| Leukemia | | | | | | |
| CCRF-CEM | 3.30 | 1.95 | 0.29 | 4.90 | 1.53 | 0.26 |
| HL-60(TB) | 3.20 | 2.07 | — | 3.84 | 1.66 | 0.29 |
| K-562 | 4.33 | 2.96 | 0.33 | 3.83 | 2.43 | 0.33 |
| MOLT-4 | 7.35 | 3.01 | 0.54 | 5.55 | 2.00 | 0.45 |
| RPMI-8226 | 3.41 | 1.39 | 0.25 | 3.60 | 0.45 | 0.26 |
| SR | 3.54 | 2.00 | 0.33 | 3.58 | 1.40 | 0.27 |
| Non-small Cell Lung | | | | | | |
| A549/ATCC | 4.74 | 1.83 | — | 5.65 | 2.73 | 0.35 |
| HOP-62 | 5.66 | 2.43 | 0.58 | 13.3 | 7.45 | 0.46 |
| HOP-92 | 1.80 | 1.32 | 0.20 | 2.31 | 1.63 | 0.18 |
| NCI-H226 | 2.58 | 1.99 | 0.35 | 12.9 | 2.33 | 0.25 |
| NCI-H23 | 5.52 | 3.90 | — | 17.3 | 6.39 | 0.70 |
| NCI-H322M | 5.58 | 2.25 | — | 14.1 | 7.30 | 0.52 |
| NCI-H460 | 3.33 | 1.98 | — | 4.11 | 2.88 | 0.29 |
| NCI-H522 | 2.00 | 1.65 | 0.27 | 2.33 | 5.11 | 0.27 |
| Colon | | | | | | |
| COLO 205 | >100 | 2.23 | — | 3.19 | 2.06 | 0.30 |
| HCC-2998 | 25.7 | 1.96 | — | 27.5 | 2.32 | 0.34 |
| HCT-116 | 5.07 | 1.64 | 0.33 | 5.17 | 2.22 | 0.34 |
| HCT-15 | 4.65 | 1.74 | — | 5.58 | 2.91 | 0.32 |
| HT-29 | 52.8 | 2.03 | — | 3.92 | 3.26 | 0.36 |
| KM12 | 3.81 | 1.79 | 0.34 | 3.32 | 2.95 | 0.32 |
| SW-620 | 3.55 | 1.92 | 0.37 | 3.29 | 2.22 | 0.35 |
| CNS | | | | | | |
| SF-268 | 5.24 | 2.27 | — | 5.33 | 2.60 | 0.38 |
| SF-539 | 2.12 | 1.68 | — | 4.57 | 2.91 | 0.20 |
| SNB-19 | 6.26 | 1.91 | — | 16.2 | 2.95 | 0.72 |
| SNB-75 | 0.94 | 1.81 | 0.34 | 3.88 | 3.69 | 0.33 |
| U251 | 4.02 | 1.67 | — | 9.93 | 3.69 | 0.34 |
| Melanoma | | | | | | |
| LOX IMVI | 5.35 | 1.89 | 0.26 | 4.61 | 0.51 | 0.32 |
| MALME-3M | 5.13 | 1.64 | — | 9.74 | 4.97 | 1.21 |
| M14 | 2.70 | 2.07 | 0.30 | 4.93 | 2.07 | 0.26 |
| MDA-MB-435 | 1.60 | 2.27 | 0.19 | 1.98 | 2.06 | 0.19 |
| SK-MEL-2 | 3.95 | 2.03 | — | 4.54 | 2.41 | 0.41 |
| SK-MEL-28 | 5.97 | 1.78 | — | 34.6 | 4.33 | 1.05 |
| SK-MEL-5 | 2.24 | 1.49 | 0.22 | 1.78 | 1.16 | 0.17 |
| UACC-257 | 6.30 | 1.56 | 0.54 | 9.74 | 2.11 | 0.43 |
| UACC-62 | 4.01 | 1.62 | 0.48 | 6.90 | 2.49 | 0.39 |
| Ovarian | | | | | | |
| IGROV1 | 4.69 | 1.96 | — | 6.08 | 2.92 | 0.40 |
| OVCAR-3 | 2.41 | 1.67 | 0.30 | 2.33 | 2.04 | 0.30 |
| OVCAR-4 | 22.8 | 1.58 | 0.48 | 12.0 | 1.95 | 0.33 |
| OVCAR-5 | 32.3 | 1.94 | — | >100 | 6.88 | 0.31 |
| OVCAR-8 | 4.39 | 1.87 | 0.35 | 9.67 | 3.05 | 0.34 |
| NCI/ADR-RES | 5.28 | 2.50 | 0.41 | 3.61 | 3.29 | 0.38 |
| SK-OV-3 | 3.38 | 3.61 | 0.34 | 5.33 | 7.55 | 0.32 |
| Renal | | | | | | |
| 786-0 | 4.88 | 2.06 | 0.36 | 5.31 | 4.08 | 0.38 |
| A498 | 2.48 | 2.34 | — | 2.63 | 1.69 | 0.22 |
| ACHN | 6.31 | 1.71 | 0.39 | 6.63 | 2.57 | 0.32 |
| CAKI-1 | 4.15 | 2.26 | — | 6.07 | 2.98 | 0.32 |
| RXF393 | 1.48 | 1.79 | 0.28 | 7.04 | 1.79 | 0.25 |
| SN12C | 5.16 | 2.08 | — | 20.5 | 3.29 | 0.39 |
| TK-10 | 8.78 | 2.19 | — | 17.3 | 4.04 | 0.43 |
| UO-31 | 3.79 | 1.43 | — | 4.09 | 3.11 | 0.31 |
| Prostate | | | | | | |
| PC-3 | 3.87 | 1.96 | 0.34 | 3.96 | 2.35 | 0.34 |
| DU-145 | 4.10 | 3.76 | — | 5.36 | 7.45 | 0.28 |

TABLE 1-continued

The GI$_{50}$ (the concentration needed to reduce the growth of treated cells to half that of untreated cells) values for compounds 4b, 4c, 4g, 4q, 4s and 4t in sixty cancer cell lines.

| Panel/ Cell line | NSC766334 4b | NSC766326 4c | NSC766320 4g | NSC766314 4q | NSC766317 4s | NSC766329 4t |
|---|---|---|---|---|---|---|
| Breast | | | | | | |
| MCF7 | 3.04 | 2.49 | 0.32 | 3.17 | 2.43 | 0.28 |
| MDA-MB-231/ATCC | 11.4 | 2.05 | — | 5.53 | 3.74 | 0.33 |
| HS578T | 3.24 | 3.46 | 0.41 | 3.67 | 7.62 | 0.24 |
| BT-549 | 7.51 | 1.71 | 0.32 | 2.99 | 1.98 | 0.35 |
| T-47D | 4.63 | 2.02 | — | 5.85 | 3.90 | 0.29 |
| MDA-MB-468 | 2.31 | 1.51 | 0.24 | 2.83 | 0.96 | 0.23 |

— not done on that cell line

From the above table it is concluded that 4g shows highest anticancer activity.

TABLE 2

The mean graph midpoint values (MG_MID) of Log$_{10}$GI$_{50}$ (log values of concentration in mol/L causing 50% inhibition of net cell growth) values for compounds 4b, 4c, 4g, 4q, 4s and 4t in sixty cancer cell lines.

| Cancer cell lines | 4b | 4c | 4g | 4q | 4s | 4t |
|---|---|---|---|---|---|---|
| Leukemia | | | | | | |
| CCRF-CEM | −5.48 | −5.71 | −6.54 | −5.31 | −5.82 | −6.58 |
| HL-60(TB) | −5.49 | −5.68 | — | −5.42 | −5.78 | −6.53 |
| K-562 | −5.36 | −5.53 | −6.47 | −5.42 | −5.61 | −6.48 |
| MOLT-4 | −5.13 | −5.52 | −6.26 | −5.26 | −5.70 | −6.34 |
| RPMI-8226 | −5.47 | −5.86 | −6.59 | −5.44 | −6.35 | −6.57 |
| SR | −5.45 | −5.70 | −6.48 | −5.45 | −5.85 | −6.56 |
| Non-small Cell Lung | | | | | | |
| A549/ATCC | −5.32 | −5.74 | — | −5.25 | −5.56 | −6.45 |
| HOP-62 | −5.25 | −5.61 | −6.23 | −4.88 | −5.13 | −6.33 |
| HOP-92 | −5.74 | −5.88 | −6.69 | −5.64 | −5.79 | −6.73 |
| NCI-H226 | −5.59 | −5.70 | −6.45 | −4.89 | −5.63 | −6.60 |
| NCI-H23 | −5.26 | −5.41 | — | −4.76 | −5.19 | −6.15 |
| NCI-H322M | −5.25 | −5.65 | — | −4.85 | −5.14 | −6.28 |
| NCI-H460 | −5.48 | −5.70 | — | −5.39 | −5.54 | −6.52 |
| NCI-H522 | −5.70 | −5.78 | −6.56 | −5.63 | −5.29 | −6.57 |
| Colon | | | | | | |
| COLO 205 | >4.00 | −5.65 | — | −5.50 | −5.69 | −6.52 |
| HCC-2998 | −4.59 | −5.71 | — | −4.56 | −5.64 | −6.46 |
| HCT-116 | −5.30 | −5.79 | −6.48 | −5.29 | −5.65 | −6.46 |
| HCT-15 | −5.33 | −5.76 | — | −5.25 | −5.54 | −6.48 |
| HT-29 | −4.28 | −5.69 | — | −5.41 | −5.49 | −6.43 |
| KM12 | −5.42 | −5.75 | −6.46 | −5.48 | −−5.53 | −6.49 |
| SW-620 | −5.45 | −5.72 | −6.42 | −5.48 | −5.65 | −6.45 |
| CNS | | | | | | |
| SF-268 | −5.28 | −5.64 | — | −5.27 | −5.58 | −6.41 |
| SF-539 | −5.67 | −5.78 | — | −5.34 | −5.54 | −6.69 |
| SNB-19 | −5.20 | −5.72 | — | −4.79 | — | −6.14 |
| SNB-75 | −6.02 | −5.74 | −6.47 | −5.41 | −5.53 | −6.47 |
| U251 | −5.40 | −5.78 | — | −5.00 | −5.43 | −6.47 |
| Melanoma | | | | | | |
| LOX IMVI | −5.27 | −5.72 | −6.58 | −5.34 | −6.29 | −6.49 |
| MALME-3M | −5.29 | −5.78 | — | −5.01 | −5.20 | −5.92 |
| M14 | −5.57 | −5.68 | −6.52 | −5.31 | −5.68 | −6.58 |
| MDA-MB-435 | −5.80 | −5.64 | −6.71 | −5.70 | −5.69 | −6.71 |
| SK-MEL-2 | −5.40 | −5.69 | — | −5.34 | −5.62 | −6.38 |
| SK-MEL-28 | −5.22 | −5.75 | — | −4.46 | −5.36 | −5.98 |
| SK-MEL-5 | −5.65 | −5.83 | −6.64 | −5.75 | −5.94 | −6.75 |
| UACC-257 | −5.20 | −5.81 | −6.27 | −5.01 | −5.68 | −6.36 |
| UACC-62 | −5.40 | −5.79 | −6.31 | −5.16 | −5.60 | −6.40 |
| Ovarian | | | | | | |
| IGROV1 | −5.33 | −5.71 | — | −5.22 | −5.53 | −6.40 |
| OVCAR-3 | −5.62 | −5.78 | −6.52 | −5.63 | −5.69 | −6.52 |
| OVCAR-4 | −5.80 | −6.32 | −6.32 | −4.92 | −5.71 | −6.47 |
| OVCAR-5 | −4.49 | −5.71 | — | >−4.00 | −5.16 | −6.51 |
| OVCAR-8 | −5.36 | −5.73 | −6.45 | −5.01 | −5.52 | −6.46 |
| NCI/ADR-RES | −5.28 | −5.60 | −6.38 | −5.44 | −5.48 | −6.42 |
| SK-OV-3 | −5.47 | −5.44 | −6.46 | −5.27 | −5.12 | −6.49 |
| Renal | | | | | | |
| 786-0 | −5.31 | −5.69 | −6.43 | −5.28 | −5.39 | −6.41 |
| A498 | −5.61 | −5.62 | — | −5.58 | −5.77 | −6.64 |
| ACHN | −5.20 | −5.77 | −6.40 | −5.18 | −5.59 | −6.49 |
| CAKI-1 | −5.38 | −5.65 | — | −5.22 | −5.53 | −6.49 |
| RXF393 | −5.83 | −5.75 | −6.55 | −5.15 | −5.75 | −6.59 |
| SN12C | −5.29 | −5.68 | — | −4.69 | −5.48 | −6.41 |
| TK-10 | −5.06 | −5.66 | — | −4.76 | −5.39 | −6.36 |
| UO-31 | −5.42 | −5.84 | — | −5.39 | −5.51 | −6.50 |
| Prostate | | | | | | |
| PC-3 | −5.41 | −5.71 | −6.46 | −5.40 | −5.63 | −6.47 |
| DU-145 | −5.39 | −5.43 | — | −5.27 | −5.13 | −6.55 |
| Breast | | | | | | |
| MCF7 | −5.52 | −5.60 | −6.49 | −5.50 | −5.61 | −6.54 |
| MDA-MB-231/ATCC | −4.94 | −5.69 | — | −5.26 | −5.43 | −6.48 |
| HS578T | −5.49 | −5.46 | −6.38 | −5.44 | −5.12 | −6.62 |
| BT-549 | −5.12 | −5.77 | −6.49 | −5.52 | −5.70 | −6.45 |
| T-47D | −5.33 | −5.70 | — | −5.23 | −5.41 | −6.53 |
| MDA-MB-468 | −5.64 | −5.82 | −6.61 | −5.55 | −6.02 | −6.63 |

From the above table it is concluded that compound 4g shows highest anticancer activity.

TABLE 3

The mean graph midpoint values (MG_MID) of Log$_{10}$ LC$_{50}$ values (log value of the concentration of compounds leading to 50% net cell death) for compounds 4b, 4c, 4g, 4q, 4s and 4t in sixty cancer cell lines.

| Cancer cell lines | Log$_{10}$ LC$_{50}$ | | | | | |
|---|---|---|---|---|---|---|
| | 4b | 4c | 4g | 4q | 4s | 4t |
| Leukemia | | | | | | |
| CCKF-CEM | >−4.00 | >−4.00 | >−4.00 | >−4.00 | >−4.00 | >−4.00 |
| HL-60(TB) | >−4.00 | >−4.00 | — | >−4.00 | −5.05 | >−4.00 |
| K-562 | >−4.00 | >−4.00 | >−4.00 | >−4.00 | >−4.00 | >−4.00 |
| MOLT-4 | >−4.00 | >−4.00 | >−4.00 | >−4.00 | >−4.00 | >−4.00 |
| RPMI-8226 | >−4.00 | >−4.00 | >−4.00 | >−4.00 | >−4.00 | — |
| SR | >−4.00 | >−4.00 | >−4.00 | >−4.00 | >−4.00 | >−4.00 |
| Non-small Cell Lung | | | | | | |
| A549/ATCC | >−4.00 | >−4.00 | >−4.00 | >−4.00 | >−4.00 | >−4.00 |
| HOP-62 | >−4.00 | >−4.00 | — | >−4.00 | >−4.00 | — |
| HOP-92 | >−4.00 | −5.05 | — | >−4.00 | −5.16 | >−4.00 |
| NCI-H226 | >−4.00 | −5.07 | — | >−4.00 | — | −5.23 |
| NCI-H23 | >−4.00 | >−4.00 | >−4.00 | >−4.00 | >−4.00 | — |
| NCI-H322M | >−4.00 | −4.56 | — | >−4.00 | >−4.00 | >−4.00 |
| NCI-H460 | >−4.00 | −5.06 | — | >−4.00 | >−4.00 | — |
| NCI-H522 | >−4.00 | −5.24 | — | −4.18 | >−4.00 | −5.31 |
| Colon | | | | | | |
| COLO 205 | >−4.00 | −5.05 | — | >−4.00 | −5.44 | −5.44 |
| HCC-2998 | >−4.00 | −5.21 | — | >−4.00 | −5.30 | −5.20 |
| HCT-116 | >−4.00 | −5.25 | — | >−4.00 | — | −5.41 |
| HCT-15 | >−4.00 | −5.11 | — | >−4.00 | >−4.00 | — |
| HT-29 | >−4.00 | −5.11 | — | >−4.00 | >−4.00 | −5.37 |
| KM12 | >−4.00 | −5.18 | — | >−4.00 | >−4.00 | −5.46 |
| SW-620 | >−4.00 | −5.13 | >−4.00 | >−4.00 | — | −5.41 |
| CNS | | | | | | |
| SF-268 | >−4.00 | −4.61 | — | >−4.00 | >−4.00 | >−4.00 |
| SF-539 | >−4.13 | −5.22 | — | >−4.00 | >−4.00 | — |
| SNB-19 | >−4.00 | −5.02 | >−4.00 | >−4.00 | >−4.00 | >−4.00 |
| SNB-75 | >−4.00 | −4.55 | — | >−4.00 | >−4.00 | — |
| U251 | >−4.00 | −5.23 | — | >−4.00 | >−4.00 | −5.09 |
| Melanoma | | | | | | |
| LOX IMVI | >−4.00 | −5.01 | — | >−4.00 | −5.51 | — |
| MALME-3M | >−4.00 | −5.11 | — | >−4.00 | >−4.00 | −5.08 |
| M14 | >−4.00 | −5.06 | — | >−4.00 | −5.36 | — |
| MDA-MB-435 | >−4.00 | >−4.00 | >−4.00 | −4.01 | >−4.00 | — |
| SK-MEL-2 | >−4.00 | −5.08 | — | >−4.00 | −5.21 | — |
| SK-MEL-28 | >−4.00 | −5.22 | — | >−4.00 | >−4.00 | — |
| SK-MEL-5 | >−4.00 | −5.26 | — | −4.74 | −5.60 | −6.12 |
| UACC-257 | >−4.00 | −5.25 | — | >−4.00 | — | −5.06 |
| UACC-62 | >−4.00 | −5.10 | — | >−4.00 | >−4.00 | −5.03 |
| Ovarian | | | | | | |
| IGROV1 | >−4.00 | −5.08 | — | >−4.00 | >−4.00 | −5.27 |
| OVCAR-3 | >−4.14 | −5.22 | — | >−4.00 | — | −5.32 |
| OVCAR-4 | >−4.00 | −5.16 | — | >−4.00 | >−4.00 | >−4.00 |
| OVCAR-5 | >−4.00 | −5.18 | — | >−4.00 | >−4.00 | — |
| OVCAR-8 | >−4.00 | −4.50 | >−4.00 | >−4.00 | >−4.00 | >−4.00 |
| NCI/ADR-RES | >−4.00 | >−4.00 | >−4.00 | >−4.00 | >−4.00 | >−4.00 |
| SK-OV-3 | >−4.00 | −4.27 | >−4.00 | >−4.00 | >−4.00 | >−4.00 |
| Renal | | | | | | |
| 786-0 | >−4.00 | −5.18 | — | >−4.00 | >−4.00 | — |
| A498 | >−4.00 | −4.62 | — | >−4.00 | −5.23 | — |
| ACHN | >−4.00 | −5.21 | — | >−4.00 | >−4.00 | — |
| CAKI-1 | >−4.00 | >−4.00 | — | >−4.00 | >−4.00 | >−4.00 |
| RXF393 | >−4.14 | −5.10 | >−4.00 | >−4.00 | −5.26 | −5.30 |
| SN12C | >−4.00 | >−4.00 | — | >−4.00 | >−4.00 | >−4.00 |
| TK-10 | >−4.00 | −5.20 | >−4.00 | >−4.00 | >−4.00 | — |
| UO-31 | >−4.00 | −5.03 | — | >−4.00 | >−4.00 | −5.16 |
| Prostate | | | | | | |
| PC-3 | >−4.00 | >−4.00 | >−4.00 | >−4.00 | >−4.00 | >−4.00 |
| DU-145 | >−4.00 | −4.41 | >−4.00 | >−4.00 | >−4.00 | — |
| Breast | | | | | | |
| MCF7 | >−4.00 | >−4.00 | >−4.00 | >−4.00 | >−4.00 | >−4.00 |
| MDA-MB-231/ATCC | >−4.00 | −4.22 | >−4.00 | >−4.00 | >−4.00 | >−4.00 |
| HS578T | >−4.00 | >−4.00 | >−4.00 | >−4.00 | >−4.00 | >−4.00 |
| BT-549 | >−4.00 | −5.18 | — | >−4.00 | −5.26 | −5.26 |
| T-47D | >−4.00 | −4.55 | — | >−4.00 | >−4.00 | — |
| MDA-MB-468 | >−4.00 | −5.06 | — | >−4.00 | −5.11 | −5.46 |

TABLE 4

The mean graph midpoint values (MG_MID) of log$_{10}$TGI (log value of concentration of the compound resulting in total inhibition of net cell growth) for compounds 4b, 4c, 4g, 4q, 4s and 4t in sixty cancer cell lines.

| Cancer cell lines | Log$_{10}$ TGI$_{50}$ | | | | | |
|---|---|---|---|---|---|---|
| | 4b | 4c | 4g | 4q | 4s | 4t |
| Leukemia | | | | | | |
| CCRF-CEM | >−4.00 | >−4.00 | — | >−4.00 | >−4.00 | — |
| HL-60(TB) | −4.52 | −5.22 | >−4.00 | −4.59 | −5.05 | −6.07 |
| K-562 | >−4.00 | −5.06 | >−4.00 | >−4.00 | −>−4.00 | >−4.00 |
| MOLT-4 | >−4.00 | −5.06 | >−4.00 | >−4.00 | >−4.00 | >−4.00 |
| RPMI-8226 | >−4.00 | −5.20 | — | >−4.00 | >−4.00 | −5.99 |
| SR | >−4.00 | −5.09 | — | >−4.00 | >−4.00 | — |
| Non-small Cell Lung | | | | | | |
| A549/ATCC | >−4.00 | −5.34 | — | >−4.00 | >−4.00 | −5.74 |
| HOP-62 | −4.25 | −5.29 | — | >−4.00 | >−4.00 | −5.72 |
| HOP-92 | −4.77 | 5.46 | — | −5.11 | −5.16 | −5.01 |
| NCI-H226 | −4.88 | −5.39 | — | >−4.00 | — | −6.15 |
| NCI-H23 | >−4.00 | −4.72 | — | >−4.00 | >−4.00 | −5.62 |
| NCI-H322M | >−4.00 | −5.15 | — | >−4.00 | >−4.00 | −5.62 |

TABLE 4-continued

The mean graph midpoint values (MG_MID) of $\log_{10}$TGI (log value of concentration of the compound resulting in total inhibition of net cell growth) for compounds 4b, 4c, 4g, 4q, 4s and 4t in sixty cancer cell lines.

| Cancer cell lines | $\log_{10}$ TGI$_{50}$ | | | | | |
|---|---|---|---|---|---|---|
| | 4b | 4c | 4g | 4q | 4s | 4t |
| NCI-H460 | −4.85 | −5.38 | — | −4.60 | >−4.00 | −6.03 |
| NCI-H522 | −5.22 | −5.51 | — | −5.20 | >−4.00 | −6.10 |
| Colon | | | | | | |
| COLO 205 | >−4.00 | −5.35 | — | −4.92 | −5.44 | −6.13 |
| HCC-2998 | >−4.00 | −5.46 | — | >−4.00 | −5.30 | −5.92 |
| HCT-116 | >−4.00 | −5.52 | — | >−4.00 | — | −5.92 |
| HCT-15 | >−4.00 | −5.43 | — | >−4.00 | >−4.00 | −5.88 |
| HT-29 | >−4.00 | −5.40 | — | −4.82 | >−4.00 | −5.96 |
| KM12 | −4.22 | −5.46 | — | −4.89 | >−4.00 | −5.97 |
| SW-620 | >−4.00 | −5.42 | — | −4.30 | — | −5.90 |
| CNS | | | | | | |
| SF-268 | −4.17 | −5.23 | — | −4.01 | >−4.00 | −5.74 |
| SF-539 | −5.21 | −5.50 | — | −4.42 | >−4.00 | −6.29 |
| SNB-19 | >−4.00 | −5.37 | — | >−4.00 | >−4.00 | — |
| SNB-75 | −4.49 | −5.14 | — | >−4.00 | >−4.00 | −5.85 |
| U251 | >−4.00 | −5.50 | — | >−4.00 | >−4.00 | −5.84 |
| Melanoma | | | | | | |
| LOX IMVI | >−4.00 | −5.37 | — | −4.19 | −5.51 | −5.99 |
| MALME-3M | >−4.00 | −5.45 | — | −4.15 | >−4.00 | −5.50 |
| M14 | −5.09 | −5.37 | — | −>−4.00 | −5.36 | −6.18 |
| MDA-MB-435 | −5.39 | −5.19 | — | −5.27 | >−4.00 | — |
| SK-MEL-2 | −4.39 | −5.39 | — | −4.66 | −5.21 | −5.80 |
| SK-MEL-28 | >−4.00 | −5.49 | — | >−4.00 | >−4.00 | −5.51 |
| SK-MEL-5 | −5.13 | −5.54 | — | −5.36 | −5.60 | −6.43 |
| UACC-257 | >−4.00 | −5.53 | — | >−4.00 | — | −5.66 |
| UACC-62 | >−4.00 | −5.44 | — | >−4.00 | >−4.00 | −5.67 |
| Ovarian | | | | | | |
| IGROV1 | −4.45 | −5.40 | — | >−4.00 | >−4.00 | −5.87 |
| OVCAR-3 | −5.24 | −5.50 | — | −5.19 | — | −6.06 |
| OVCAR-4 | >−4.00 | −5.48 | — | −4.04 | >−4.00 | −5.46 |
| OVCAR-5 | >−4.00 | −5.45 | — | >−4.00 | >−4.00 | −5.97 |
| OVCAR-8 | −4.33 | −5.33 | — | >−4.00 | >−4.00 | — |
| NCI/ADR-RES | >−4.00 | −5.16 | — | −4.46 | >−4.00 | −5.75 |
| SK-OV-3 | −4.54 | −4.87 | — | −4.11 | >−4.00 | −6.03 |
| Renal | | | | | | |
| 786-0 | >−4.30 | −5.43 | — | >−4.00 | >−4.00 | −5.88 |
| A498 | −5.16 | −5.24 | — | −5.01 | −5.23 | −6.14 |
| ACHN | >−4.00 | −5.49 | — | >−4.00 | >−4.00 | −5.89 |
| CAKI-1 | >−4.00 | −5.21 | — | >−4.00 | >−4.31 | −5.81 |
| RXF393 | −5.36 | −5.42 | — | >−4.00 | −5.26 | −6.07 |
| SN12C | >−4.00 | −5.25 | — | >−4.00 | >−4.00 | −5.67 |
| TK-10 | −4.16 | −5.43 | — | −4.20 | >−4.00 | −5.82 |
| UO-31 | −4.47 | −5.44 | — | >−4.00 | >−4.00 | −5.78 |
| Prostate | | | | | | |
| PC-3 | −4.32 | −5.20 | — | >−4.00 | >−4.00 | −5.76 |
| DU-145 | −4.12 | −4.92 | — | >−4.00 | >−4.00 | −6.15 |
| Breast | | | | | | |
| MCF7 | >−4.00 | −4.99 | — | >−4.00 | >−4.00 | — |
| MDA-MB-231/ATCC | >−4.00 | −5.26 | — | >−4.00 | >−4.00 | −5.93 |
| HS578T | −4.52 | >−4.00 | >−4.00 | −4.64 | >−4.00 | — |
| BT-549 | −4.06 | −5.47 | — | −5.00 | −5.26 | −5.87 |
| T-47D | >−4.00 | −5.30 | — | >−4.00 | >−4.00 | −6.05 |
| MDA-MB-468 | −5.15 | −5.44 | — | >−4.00 | −5.11 | −6.05 |

ADVANTAGES OF THE INVENTION

1. The present invention provides 3-(4-ethynylphenyl)pyridopyrimidinone compounds of formula A.

2. It also provides a process for the preparation of 3-(4-ethynylphenyl)pyridopyrimidinone compounds of formula A.

We claim:

1. A compound selected from the group consisting of:
(E)-3-(4-Ethynylphenyl)-2-(4-fluorostyryl)pyrido[2,3-d]pyrimidin-4(3H)-one (4a);
(E)-3-(4-Ethynylphenyl)-2-(4-hydroxystyryl)pyrido[2,3-d]pyrimidin-4(3H)-one (4b);

(E)-3-(4-Ethynylphenyl)-2-(4-(trifluoromethyl)styryl) pyrido[2,3-d]pyrimidin-4(3H)-one (4c);

(E)-3-(4-Ethynylphenyl)-2-(3-(trifluoromethoxy)styryl) pyrido[2,3-d]pyrimidin-4(3H)-one (4d);

(E)-2-(4-Chlorostyryl)-3-(4-ethynylphenyl)pyrido[2,3-d] pyrimidin-4(3H)-one (4e);

(E)-2-(3,4-Difluorostyryl)-3-(4-ethynylphenyl)pyrido[2, 3-d]pyrimidin-4(3H)-one (4f);

(E)-2-(4-Chloro-3-fluorostyryl)-3-(4-ethynylphenyl) pyrido[2,3-d]pyrimidin-4(3H)-one (4g);

(E)-3-(4-Ethynylphenyl)-2-(3-fluoro-4-methoxystyryl) pyrido[2,3-d]pyrimidin-4(3H)-one (4h);

(E)-2-(2,4-Dihydroxystyryl)-3-(4-ethynylphenyl)pyrido [2,3-d]pyrimidin-4(3H)-one (4i), (E)-2-(2,5-Dihydroxystyryl)-3-(4-ethynylphenyl)pyrido [2,3-d]pyrimidin-4(3H)-one(4j);

(E)-3-(4-Ethynylphenyl)-2-(4-hydroxy-3-methoxystyryl) pyrido[2,3-d]pyrimidin-4(3H)-one (4k);

(E)-3-(4-Ethynylphenyl)-2-(4-hydroxy-3-nitrostyryl) pyrido[2,3-d]pyrimidin-4(3H)-one (4l);

(E)-2-(3,5-Dimethoxystyryl)-3-(4-ethynylphenyl)pyrido [2,3-d]pyrimidin-4(3H)-one (4m);

(E)-2-(2,5-Dimethoxystyryl)-3-(4-ethynylphenyl)pyrido [2,3-d]pyrimidin-4(3H)-one (4n);

(E)-3-(4-Ethynylphenyl)-2-(4-hydroxy-3,5-dimethyl-styryl)pyrido[2,3-d]pyrimidin-4(3M-one (4p);

(E)-3-(4-Ethynylphenyl)-2-(3,4,5-trimethoxystyryl) pyrido[2,3-d]pyrimidin-4(3M-one (4q);

(E)-3-(4-Ethynylphenyl)-2-(2,4,6-trimethoxystyryl) pyrido[2,3-d]pyrimidin-4(3M-one (4r);

(E)-3-(4-Ethynylphenyl)-2-(2-(naphthalen-2-yl)vinyl) pyrido[2,3-d]pyrimidin-4(3M-one (4s);

(E)-3-(4-Ethynylphenyl)-2-(2-(quinolin-2-yl)vinyl) pyrido[2,3-d]pyrimidin-4(3H)-one (4t);

(E)-3-(4-Ethynylphenyl)-2-(2-(5-methoxy-1H-indol-3-yl)vinyl)pyrido[2,3-d]pyrimidin-4(3H)-one (4v);

(E)-3-(4-Ethynylphenyl)-2-(2-(5-nitrofuran-2-yl)vinyl) pyrido[2,3-d]pyrimidin-4(3H)-one (4w); and (E)-3-(4-Ethynylphenyl)-2-(2-(5-nitrothiophen-2-yl)vi-nyl)pyrido[2,3-d]pyrimidin-4(3H)-one(4x).

2. A compound selected from the group consisting of:

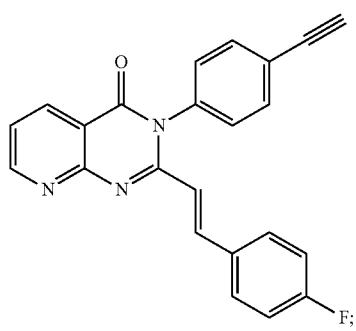

4a

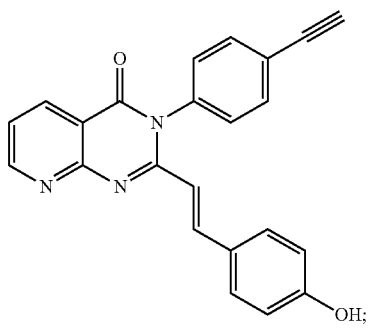

4b

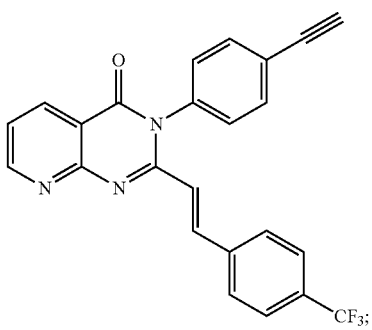

4c

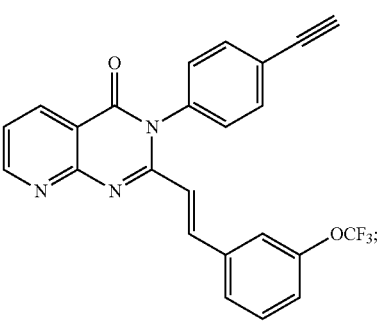

4d

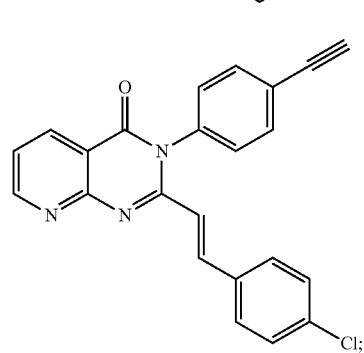

4e

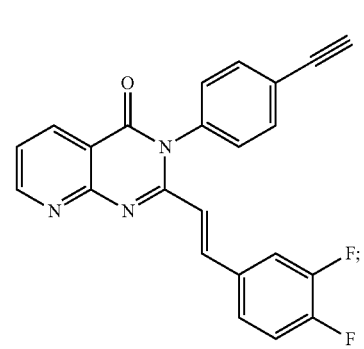

4f

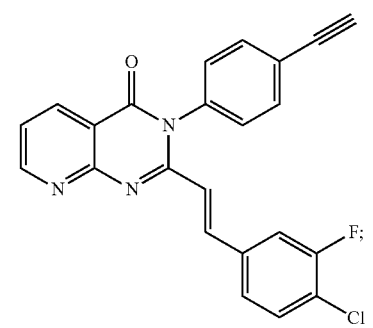
4g
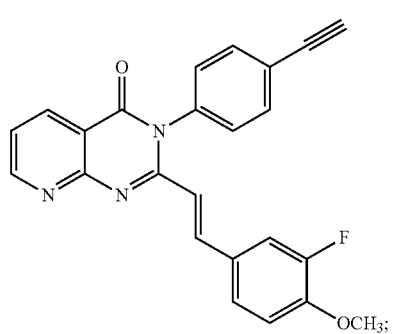
4h
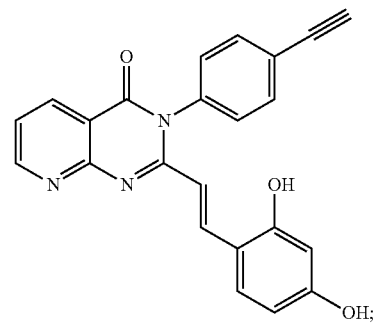
4i
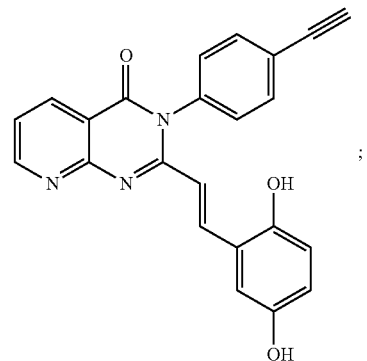
4j
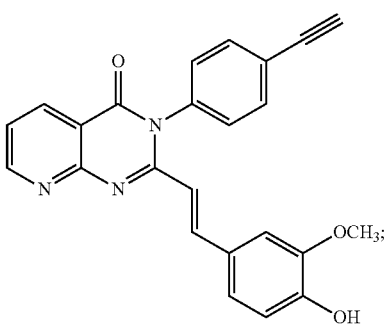
4k
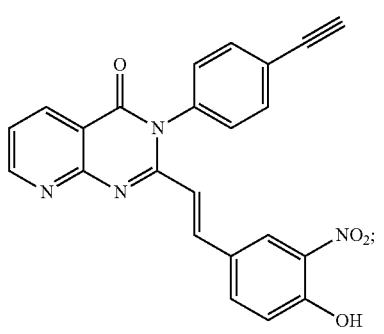
4l
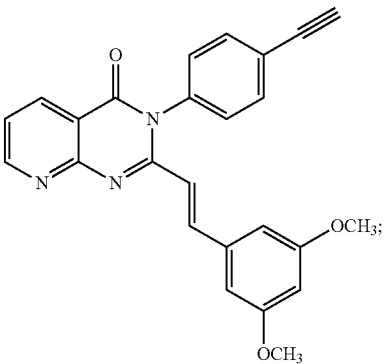
4m
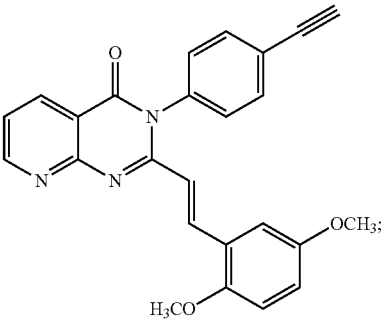
4n

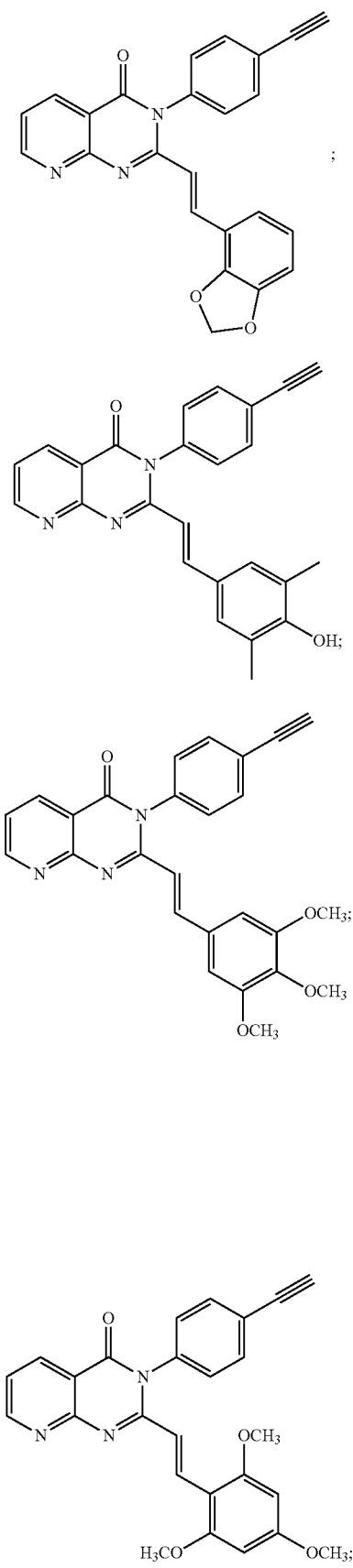
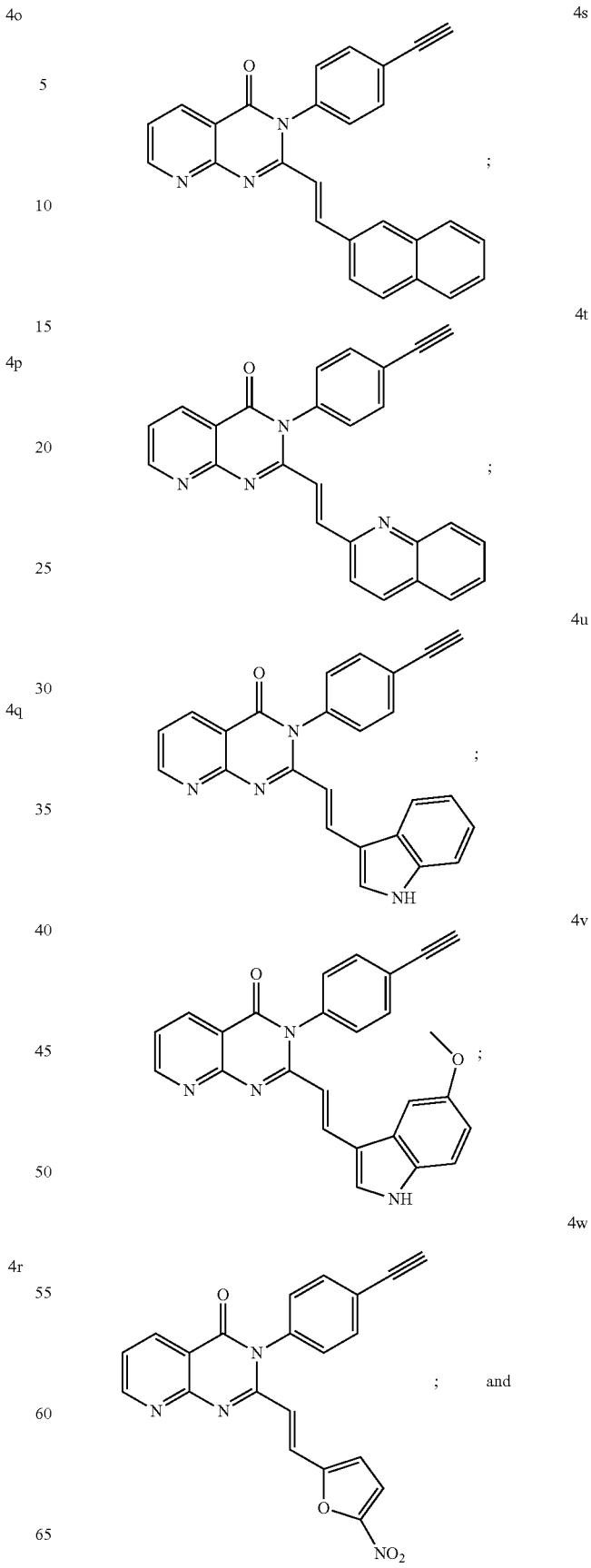

3. A compound selected from the group consisting of structural formula:

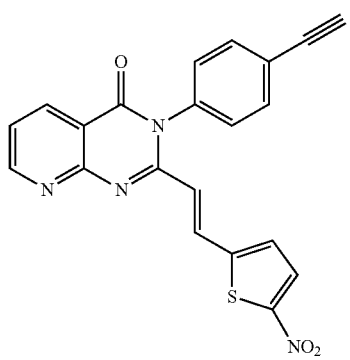
4x

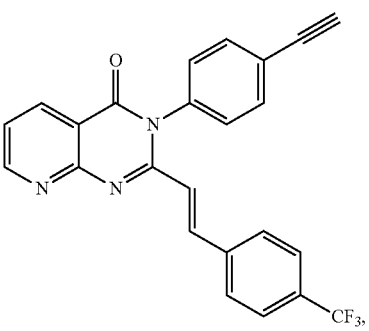
4b

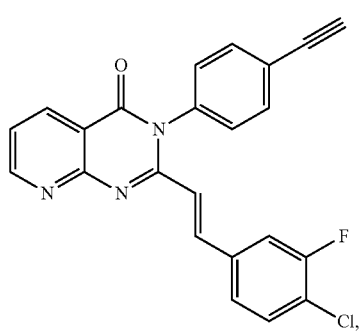
4c

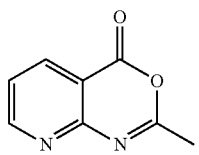
4g

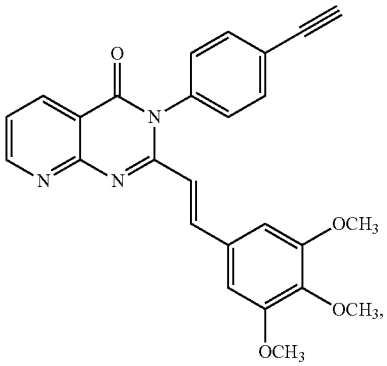
4q

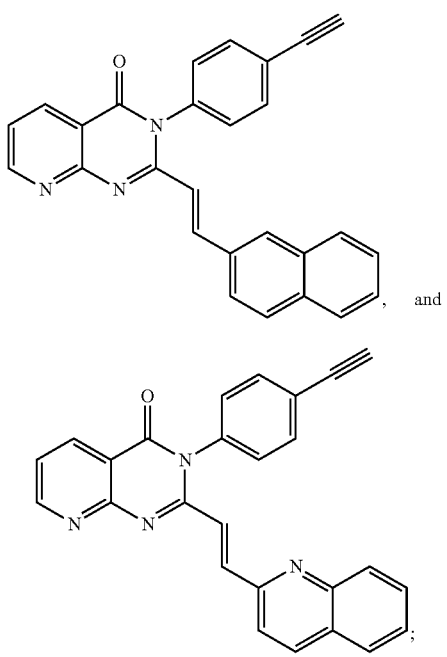
4s

, and

4t wherein the compound exhibits an in vitro anticancer activity against human cancer cell lines selected from the group consisting of leukemia cell line, non small cell lung cell line, colon cell line, CNS cell line, renal cell line, prostate cell line, ovarian cell line, breast cell line, and melanoma cell line.

4. A process for the preparation of the compound as claimed in claim 2, said process comprising the steps of:

a. reacting 2-aminonicotinic acid with acetic anhydride at reflux temperature for a time period in the range of 10 to 45 minutes to obtain 2-methyl-4H-pyrido[2,3-d][1,3]oxazin-4-one (6),

6 b. reacting 2-methyl-4H-pyrido[2,3-d][1,3]oxazin-4-one (6) obtained in step (a) with 4-ethynylaniline (7) in an organic solvent under reflux conditions for a time period in the range of 2 to 10 hours to obtain 2-methyl3-(4-ethynylphenyl)-2-methylpyrido[2,3-d]pyrimidin-4(3H)-one (8),

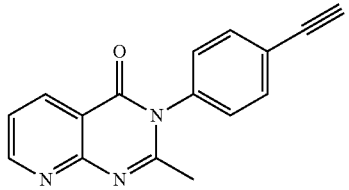

c. reacting 2-methyl3-(4-ethynylphenyl)-2-methylpyrido[2,3-d]pyrimidin-4(3H)-one (8) obtained in step (b) with a substituted aldehyde in an organic solvent under reflux conditions for a time period in the range of 6 to 10 hours to obtain the desired products of formulae 4a-n, 4p-4t, and 4v-4x.

5. The process as claimed in claim 4, wherein the organic solvent used in step (b) and (c) is selected from the group consisting acetic acid, propionic acid, and DMF.

6. The process as claimed in claim 4, wherein the substituted aldehyde used in step (c) is selected from the group consisting of 3,4,5-trimethoxybenzaldehyde, 2,4,6-trimethoxy benzaldehyde, 2,5-dimethoxybenzaldehyde, 3,5-dimethoxybenzaldehyde, quinoline-2-carboxaldehyde, 2-naphthaldehyde, 4-fluorobenzaldehyde, 3,4-difluoro benzaldehyde, 4-hydroxybenzaldehyde, 5-methoxy-indole-3-carboxaldehyde, 3-methoxy-4-hydroxybenzaldehyde, piperonal, 3-fluoro-4-methoxy benzaldehyde, 3-fluoro-4-chlorobenzadehyde, 4-trifluoromethylbenzaldehyde, 3-trifluoromethoxybenzaldehyde, 4-chlorobenzaldehyde, 2,4-dihydroxy benzaldehyde, and 2,5-dihydroxybenzaldehyde.

7. The process as claimed in claim 4, wherein the reflux temperature in step (a) is in the range of 150-155° C.

8. The process as claimed in claim 4, wherein the reflux temperature in step (b) and (c) is in the range of 120-125° C.

9. The process as claimed in claim 4, wherein the yield of obtaining the products of formulae 4a-n, 4p-4t, and 4v-4x is in the range of 85-90%.

* * * * *

UNITED STATES PATENT AND TRADEMARK OFFICE
CERTIFICATE OF CORRECTION

| | |
|---|---|
| PATENT NO. | : 9,783,537 B2 |
| APPLICATION NO. | : 14/912755 |
| DATED | : October 10, 2017 |
| INVENTOR(S) | : Kamal et al. |

It is certified that error appears in the above-identified patent and that said Letters Patent is hereby corrected as shown below:

In the Claims

In Claim 1, Column 41, Line 30, in the listing of compound 4p, replace the term "4(3M-one" with --4(3H)-one--

In Claim 1, Column 41, Line 33, in the listing of compound 4q, replace the term "4(3M-one" with --4(3H)-one--

In Claim 1, Column 41, Line 35, in the listing of compound 4r, replace the term "4(3M-one" with --4(3H)-one--

In Claim 1, Column 41, Line 38, in the listing of compound 4s, replace the term "4(3M-one" with --4(3H)-one--

In Claim 2, Column 46, Lines 30-40, delete compound 4u

In Claim 6, Column 50, Lines 8-9, delete "piperonal" from the list of substituted aldehydes Signed and Sealed this
Thirteenth Day of March, 2018

Andrei Iancu
*Director of the United States Patent and Trademark Office*